United States Patent [19]

Büttelmann et al.

[11] Patent Number: 5,688,803
[45] Date of Patent: Nov. 18, 1997

[54] TRICYCLIC DICARBONYL DERIVATIVES

[75] Inventors: Bernd Büttelmann, Schopfheim, Germany; Thierry Godel, Basel, Switzerland; Laurence Gross, Herrlisheim; Marie-Paule Heitz Neidhart, Bartenheim, both of France; Claus Riemer, Schliengen, Germany; René Wyler, Zürich, Switzerland

[73] Assignee: Hoffmann-La Roche Inc., Nutley, N.J.

[21] Appl. No.: 737,240

[22] PCT Filed: May 16, 1995

[86] PCT No.: PCT/EP95/01856

§ 371 Date: Nov. 15, 1996

§ 102(e) Date: Nov. 15, 1996

[87] PCT Pub. No.: WO95/32205

PCT Pub. Date: Nov. 30, 1995

[30] Foreign Application Priority Data

May 24, 1994 [CH] Switzerland .............. 1602/94
Feb. 17, 1995 [CH] Switzerland .............. 477/95

[51] Int. Cl.$^6$ .............. C07D 487/04; A61K 31/505
[52] U.S. Cl. .............. 514/267; 544/251; 544/60; 544/115; 544/234; 514/228.5; 514/233.2; 514/228.2; 514/248; 514/293; 546/82; 546/83; 546/84
[58] Field of Search .............. 544/251; 514/267

[56] References Cited

U.S. PATENT DOCUMENTS 4,472,400  9/1984  Tully et al. .............. 424/251
4,713,383  12/1987  Francis et al. .............. 514/267

FOREIGN PATENT DOCUMENTS 0 459 561  12/1991  European Pat. Off. .

Primary Examiner—Mukund J. Shah
Assistant Examiner—King Lit Wong
Attorney, Agent, or Firm—George W. Johnston; Ellen Ciambrone Coletti; Robert A. Silverman

[57] ABSTRACT

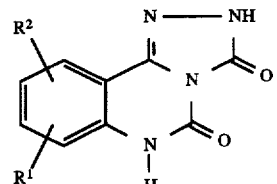
(Ia)

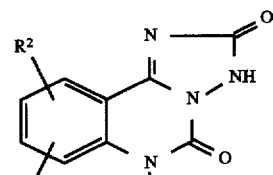

(Ib)

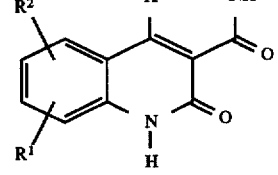

(II)

Compounds of general formula (Ia), (Ib) and (II), wherein $R^1$ and $R^2$ each independently signify hydrogen, lower alkyl, lower alkoxy, nitro, trifluoromethyl, amino, halogen, cyano or $R^3R^4NS(O)_2$— and $R^3$ and $R^4$ signify lower alkyl, and $R^2$ can additionally signify morpholino or thiomorpholino, a 5- or 6-membered heterocycle with 1–3N atoms optionally substituted by lower alkyl, hydroxy, amino or the group —$CH_2NHCH_3$, a bicyclic heterocycle with 1–3N atoms or a group —$NR^5R^6$ or —$OR^5$ in which $R^5$ and $R^6$ can be the same or different and signify hydrogen, lower alkyl, hydroxy-lower alkyl, lower alkoxy-lower alkyl, amino-lower alkyl or lower alkylamino-lower alkyl, and X in formula (II) signifies —CH=CH—, —CH=N—, —NH—, —CO— or —O—, as well as pharmaceutically usable salts of compounds of general formula (Ia), (Ib) and (II). They can be used for the treatment or prevention of illnesses, especially for the treatment or prevention of ischemia, hypoglycaemia, hypoxia, cerebral vascular spasms, spasticity, trauma, hemorrhagia, infection (viral, bacterial, amoebic, prional), epileptic seizures, autoimmune diseases, withdrawal symptoms, Alzheimer's disease, Parkinson's disease, amyotrophic lateral sclerosis, Huntington's disease, intoxications, olivoponto-cerebellar atrophy, spinal cord injuries, schizophrenia, depressions, anxiety states, dependence, pains, autism and mental retardation.

16 Claims, No Drawings

TRICYCLIC DICARBONYL DERIVATIVES

This is a 371 application of PCT/EP95/01856, filed May 16, 1995. The present invention is concerned with tricyclic dicarbonyl derivatives of the general formulae

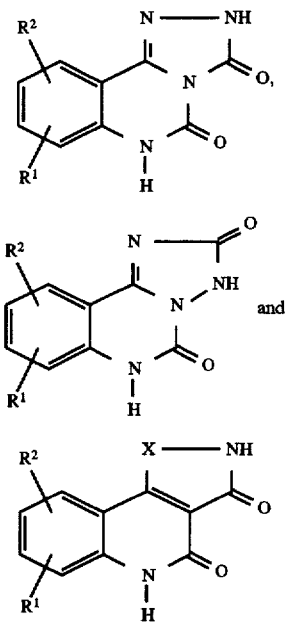

wherein
- R¹ and R² each independently signify hydrogen, lower alkyl, lower alkoxy, nitro, trifluoromethyl, amino, halogen, cyano or R³R⁴NS(O)₂— and R³ and R⁴ signify lower alkyl, and
- R² can additionally signify morpholino or thiomorpholino, a 5- or 6-membered heterocycle with 1–3N atoms optionally substituted by lower alkyl, hydroxy, amino or the group —CH₂NHCH₃, a bicyclic heterocycle with 1–3N atoms or a group —NR⁵R⁶ or —OR⁵ in which R⁵ and R⁶ can be the same or different and signify hydrogen, lower alkyl, hydroxy-lower alkyl, lower alkoxy-lower alkyl, amino-lower alkyl or lower alkylamino-lower alkyl, and
- X in formula II signifies —CH=CH—, —CH=N—, —NH—, —CO— or —O—, as well as pharmaceutically usable salts of compounds of general formulae Ia, Ib and II.

These compounds and salts are novel with the exception of 2,3,5,6-tetrahydro-[1,2,4]triazolo[1,5-c]quinazoline-2,5-dione, and it has been found that they possess valuable pharmaco-dynamic properties as non-competitive and/or AMPA/KA-R antagonists, so that they can be used as neuroprotectives, especially for the treatment or prevention of ischemia, hypoglycaemia, hypoxia, cerebral vascular spasms, spasticity, trauma, hemorrhagia, infections (viral, bacterial, amoebic, prional), epileptic seizures, autoimmune diseases, withdrawal symptoms, Alzheimer's disease, Parkinson's disease, amyotrophic lateral sclerosis, Huntington's disease, intoxications, olivopontocerebellar atrophy, spinal cord injuries, schizophrenia, depressions, anxiety states, dependence, pains, autism and mental retardation.

Objects of the present invention are the compounds defined earlier and pharmaceutically acceptable salts per se and as therapeutically active substances, a process for the manufacture of these novel compounds and salts, medicaments containing such a compound or a salt thereof, the production of such medicaments, the use of the compounds and salts defined earlier as neuroprotectives, especially in the control or prevention of ischemia, hypoglycaemia, hypoxia, cerebral vascular spasms, spasticity, trauma, hemorrhagia, infections (viral, bacterial, amoebic, prional), epileptic seizures, autoimmune diseases, withdrawal symptoms, Alzheimer's disease, Parkinson's disease, amyotrophic lateral sclerosis, Huntington's disease, intoxications, olivoponto-cerebellar atrophy, spinal cord injuries, schizophrenia, depressions, anxiety states, dependence, pains, autism and mental retardation, and the use of the compounds and salts defined earlier for the production of medicaments.

The term "lower" denotes compounds or groups with a maximum of 7, preferably a maximum of 4, carbon atoms.

The term "alkyl" denotes straight-chain or branched saturated hydrocarbon groups such as methyl, ethyl, propyl and the like.

The term "alkoxy" denotes alkyl groups in the sense of the foregoing definition which are bonded via an oxygen atom, such as methoxy and the like.

The term "halogen" signifies fluorine, chlorine, bromine and iodine.

The term "5- or 6-membered heterocycle" denotes cyclic saturated or unsaturated ring systems such as, for example, pyrrolyl, pyrrolidinyl, imidazolyl, pyrazolyl, pyrazolinyl, pyrazolidinyl, triazolyl, pyrimidinyl, piperazinyl, piperidinyl and the like, with the ring system being optionally substituted by lower alkyl, hydroxy, amino or a group —CH₂NHCH₃.

The term "bicyclic heterocycle" denotes a ring system consisting of two rings which are condensed with one another, with one of the rings being a heterocycle and the second ring being especially a benzene ring, for example a quinoxalinyl group.

The term "pharmaceutically acceptable salts" embraces salts with inorganic and organic acids such as hydrochloric acid, hydrobromic acid, nitric acid, sulphuric acid, phosphoric acid, citric acid, formic acid, fumaric acid, maleic acid, acetic acid, succinic acid, tartaric acid, methanesulphonic acid, p-toluenesulphonic acid and the like as well as salts with inorganic bases such as sodium or potassium hydroxide. Such salts can be manufactured readily by any person skilled in the art having regard to the state of the art and taking into consideration the nature of the compound to be converted into a salt.

The compounds of formulae Ia, Ib and II in accordance with the invention can also be present as tautomers, with the invention also embracing all isomers as well as mixtures thereof.

In formula Ia there are preferred compounds in which R¹ and R² each signify hydrogen, halogen, nitro, methyl or methoxy, especially the following compounds:

8,9-Dichloro-2,3,5,6-tetrahydro-1,2,4-triazolo[4,3-c]quinazoline-3,5-dione;
9-chloro-8-nitro-2,3,5,6-tetrahydro-1,2,4-triazolo[4,3-c]quinazoline-3,5-dione;
9-bromo-8-nitro-2,3,5,6-tetrahydro-1,2,4-triazolo[4,3-c]quinazoline-3,5-dione;
8,10-dichloro-2,3,5,6-tetrahydro-1,2,4-triazolo[4,3-c]quinazoline-3,5-dione;
8,9-dimethyl-2,3,5,6-tetrahydro-1,2,4-triazolo[4,3-c]quinazoline-3,5-dione
8-methoxy-2,3,5,6-tetrahydro-1,2,4-triazolo[4,3-c]quinazoline-3,5-dione;
8-iodo-2,3,5,6-tetrahydro-1,2,4-triazolo[4,3-c]quinazoline-3,5-dione;

8-chloro-9-fluoro-2,3,5,6-tetrahydro-1,2,4-triazolo[4,3-c]-quinazoline-3,5-dione;

8,9-dinitro-2,3,5,6-tetrahydro-1,2,4-triazolo[4,3-c] quinazoline-3,5-dione; and 8-nitro-2,3,5,6-tetrahydro-1,2,4-triazolo[4,3-c] quinazoline-3,5-dione.

Furthermore, the compounds of formula Ia in which $R^1$ signifies nitro and $R^2$ signifies pyrrolidinyl or dimethylamino are preferred. These are especially the following compounds:

9-Dimethylamino-8-nitro-2,3,5,6-tetrahydro-1,2,4-triazolo[4,3-c]quinazoline-3,5-dione; and 8-nitro-9-pyrrolidin-1-yl-2,3,5,6-tetrahydro-1,2,4-triazolo[4,3-c]quinazoline-3,5-dione.

The following are especially preferred compounds of formula Ib:

9-Chloro-8-nitro-2,3,5,6-tetrahydro-[1,2,4]triazolo[1,5-c]-quinazoline-2,5-dione; and 9-imidazol-1-yl-8-nitro-2,3,5,6-tetrahydro-[1,2,4]triazolo [1,5-c]quinazoline-2,5-dione.

Preferred compounds of general formula II are those in which $R^1$ and $R^2$ each signify hydrogen, halogen or nitro, especially the following compounds:

7-Chloro-2,3,4,5-tetrahydro-isoxazolo[4,5-c]quinoline-3,4-dione;

7-nitro-2,3,4,5-tetrahydro-isoxazolo[4,5-c]quinoline-3,4-dione;

7,8-dichloro-4-hydroxy-2,3-dihydro-1H-pyrazolo[4,3-c] quinoline-3-one; and 7-chloro-4-hydroxy-2,3-dihydro-1H-pyrazolo[4,3-c] quinoline-3-one.

The compounds of general formulae Ia, Ib and II can be manufactured by a) cyclizing a compound of the general formula

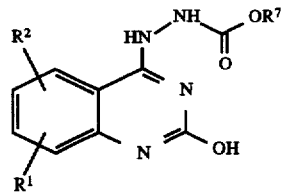

III wherein $R^1$ and $R^2$ have the significance given above and $R^7$ signifies lower alkyl, to compounds of general formula Ia, or b) rearranging a compound of general formula Ia with a suitable base in a protic solvent to compounds of general formula Ib, or c) reacting a compound of general formula III in which $R^1$ signifies $NO_2$ and $R^2$ signifies F with a corresponding heterocycle to give compounds of formula Ia in which $R^1$ signifies $NO_2$ and $R^2$ signifies a 5- or 6-membered heterocycle with 1–3N atoms optionally substituted by lower alkyl, hydroxy, amino or the group —$CH_2NHCH_3$, or d) cyclizing a compound of the general formula

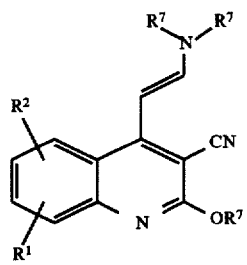

IV wherein $R^1$, $R^2$ and $R^7$ have the significance set forth above, to compounds of general formula II in which X signifies —CH=CH—, or e) reacting a compound of the general formula

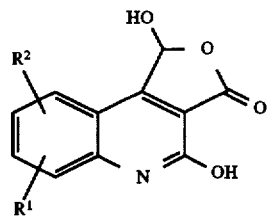

V wherein $R^1$ and $R^2$ have the significance set forth above, with hydrazine hydrate to give compounds of general formula II in which X signifies —CH=N—, or f) subjecting a compound of the general formula

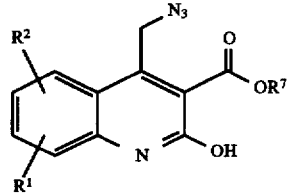

VI wherein $R^1$, $R^2$ and $R^7$ have the significance set forth above, to hydrogenation in the presence of a catalyst, cyclization and spontaneous oxidation with oxygen to give compounds of general formula II in which X signifies —CO—, or g) cyclizing a compound of the general formula

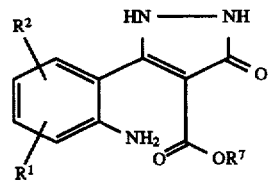

VII wherein $R^1$, $R^2$ and $R^7$ have the significance set forth above, to give compounds of general formula II in which X signifies —NH—, or h) cyclizing a compound of the general formula

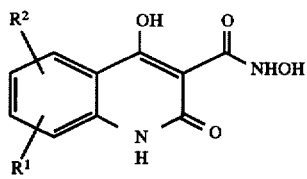

wherein $R^1$ and $R^2$ have the significance set forth above, to compounds of general formula II in which X signifies —O—, and i) if desired, converting a compound of formulae Ia, Ib or II obtained into a pharmaceutically acceptable salt.

Compounds of general formula Ia can be manufactured according to process variant a) by cyclizing a compound of general formula III in which $R^1$ and $R^2$ have the significance set forth above. This is conveniently effected by boiling at reflux temperature in a suitable solvent, for example in dimethylformamide.

Compounds of general formula Ib are obtained according to process variant b) by Dimroth rearrangement of a compound of general formula Ia. This is conveniently effected in the presence of a strong base, for example with NaOH, and in a protic solvent, for example dimethyl sulphoxide.

Compounds of general formula Ia in which the phenyl ring is substituted by a heterocycle and $NO_2$ are obtained according to process variant c). Starting from a compound of formula III in which $R^1$ signifies $NO_2$ and $R^2$ signifies F, the reaction is effected with a corresponding heterocycle by boiling for several hours in a solvent, for example in an alcohol.

Compounds of general formula II in which X is —CH=CH— and $R^1$ and $R^2$ signify the same as described above can be prepared according to process variant d) by cyclizing a compound of formula IV. This is conveniently effected by boiling under reflux conditions in an acidic-aqueous reaction mixture, with a mixture of sulphuric acid, acetic acid and water being especially preferred in this case.

The compounds of general formula II in which X signifies —CH=N— and the substituents $R^1$ and $R^2$ have the significance given above can be prepared according to process variant e). Thus, a compound of general formula V is dissolved in a solvent, for example in dimethyl sulphoxide, conveniently under a protective gas atmosphere, and subsequently, after the addition of hydrazine hydrate, stirred for a long period at room temperature.

Compounds of general formula II in which X signifies —CO— and $R^1$ and $R^2$ have the above significance are obtained according to process variant f). This is conveniently carried out by hydrogenating an azide of formula VI in the presence of a catalyst. Platinum or palladium catalysts are suitable. The catalytic hydrogenation is effected in a hydrogen stream at room temperature after a compound of general formula VI has been dissolved in a solvent mixture consisting of an alcohol, for example methanol, and dimethylformamide. The desired compound of general formula II is obtained after oxidation of a dimethylformamide solution in an oxygen stream.

Where X in formula II signifies —NH—, these compounds can be prepared according to process variant g), which can be carried out in a similar manner to that described under a). A compound of formula VII is conveniently cyclized to a compound of formula II by boiling at the reflux temperature in a suitable solvent, for example dimethylformamide.

Furthermore, compounds of general formula II in which X signifies —O— and $R^1$ and $R^2$ have the significance given above are obtained by cyclizing a compound of general formula VIII. This is conveniently carried out according to process variant h) by suspending a corresponding compound of formula VIII in tetrahydrofuran and subsequently treating with thionyl chloride. The compounds of formula II in accordance with the invention result after the addition of a base, for example of triethylamine.

Compounds of general formulae Ia, Ib and II can be converted into pharmaceutically acceptable salts according to process variant i). There come into consideration not only salts with inorganic acids, but also salts with organic acids and with inorganic bases. Examples of such salts are hydrochlorides, hydrobromides, nitrates, sulphates, phosphates, citrates, formates, fumarates, maleates, acetates, succinates, tartrates, methanesulphonates, p-toluenesulphonates as well as sodium or potassium salts and the like. These salts can be manufactured according to methods which are known per se and which will be familiar to any person skilled in the art.

The compounds used as starting materials can be prepared, for example, according to the following Reaction Schemes and the explanations of the different reactions following them.

Scheme 1

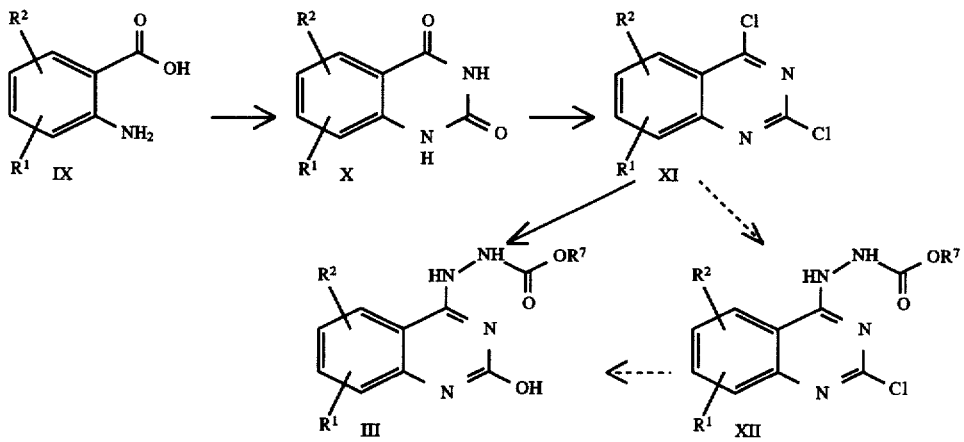

$R^1$, $R^2$ and $R^7$ have the significances given above.

Starting materials for the manufacture of compounds of general formula Ia in accordance with the invention can be prepared according to Scheme 1.

A compound of formula X can be prepared conveniently by reacting a 2-aminobenzoic acid substituted by $R^1$ and $R^2$ with urea by heating for several hours. The thus-obtained quinazolinedione of formula X is subsequently converted with a halogenating agent, preferably with phosphorus oxychloride, into the compound XI by stirring the reaction mixture at the reflux temperature for several hours. A compound of formula IIIa results upon reacting a compound of formula XI with an alkyl carbazate in dimethyl sulphoxide. Depending on the nature of the substituents $R^1/R^2$ this can be effected directly (e.g. where $R^1$ signifies alkyl or alkoxy) or via the compounds of formula XII (e.g. when $R^1$ signifies halogen). The reaction temperature can vary between 70° and 95°. Subsequently, the thus-obtained compound of formula III can be converted as described in process variant a) into the compounds of formula Ia in accordance with the invention.

Starting materials for compounds of general formula II in accordance with the invention in which X signifies —CH=CH— can be prepared according to Scheme 2.

A (2-amino-phenyl)-alkanone of formula XIII is converted while heating and stirring for several hours with an alkyl cyanoacetate into the compounds of general formula XIV. The thus-obtained 2-hydroxyquinoline-3-carbonitrile of general formula XIV is subsequently chlorinated according to generally usual methods, for example with phosphorus oxychloride, to give the compounds of formula XV which are subsequently suspended in an alcohol, treated with sodium and boiled under reflux conditions for several hours. The thus-obtained compound of general formula XVI is conveniently then reacted with N,N-dimethylformamide formamide dialkyl acetal for a few hours under reflux temperature to give the compounds of general formula IV. The thus-obtained intermediates can then be cyclized according to the described process variant d) to give the corresponding compounds of general formula II in accordance with the invention.

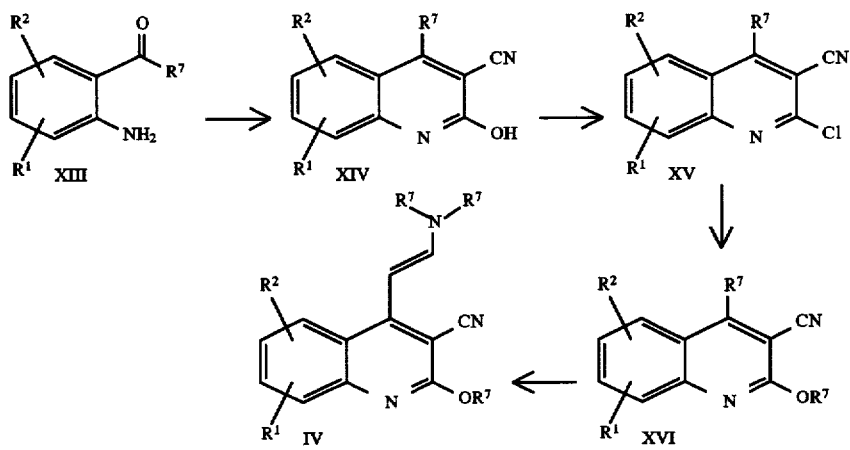

Scheme 2

$R^1$, $R^2$ and $R^7$ have the significance given above.

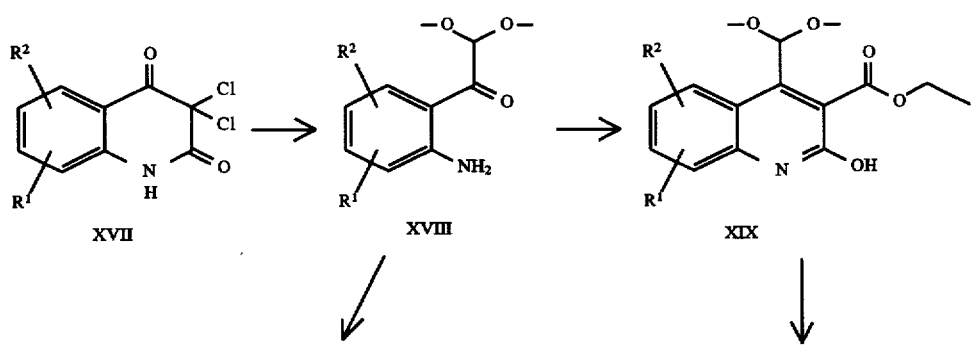

Scheme 3

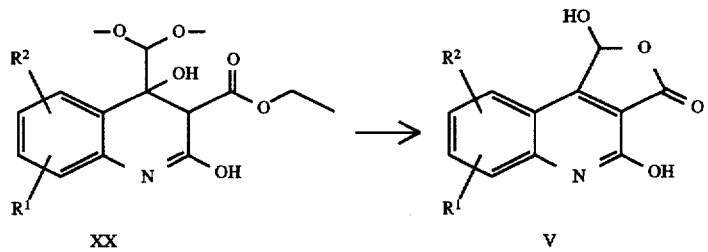

$R^1$ and $R^2$ have the significance given above.

Starting materials for the manufacture of compounds of general formula II in accordance with the invention in which X signifies —CH=N— are obtained according to Scheme 3.

Compounds of formula XVIII can be conveniently prepared by dissolving sodium in methanol, preferably under a protective gas atmosphere, and, after the addition of a methanolic solution of a corresponding 3,3-dichloro-quinolinedione derivative, converting into the compounds of formula XVIII. Subsequently, this compound is conveniently suspended in diethyl malonate and stirred under reflux conditions for several hours. The thus-obtained carboxylic acid ester of general formula XIX is subsequently conveniently treated with hydrochloric acid to give compounds of general formula V.

A further possibility for the preparation of the compounds of general formula V comprises dissolving a compound of formula XVIII in a solvent, preferably dichloromethane, treating the solution with triethylamine and ethylmalonyl chloride and stirring for several minutes while cooling. The thus-obtained compound of formula XX is subsequently conveniently stirred in a mixture consisting of acetic acid, water and sulphuric acid under reflux conditions for several hours to give compounds of general formula V.

The compounds of formula V serve as starting materials for the manufacture of compounds of general formula II in accordance with the invention according to process variant e).

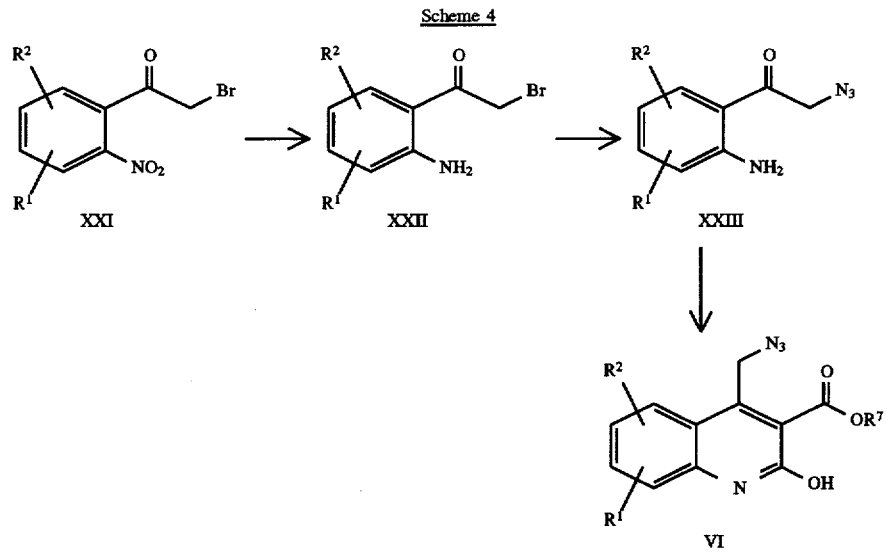

$R^1$, $R^2$ and $R^7$ have the significance given above.

Starting materials for the manufacture of compounds of general formula II in accordance with the invention in which X signifies —CO— can be obtained according to Scheme 4.

The nitro compounds of formula XXI, prepared according to "Helv. Chem. Acta, 1937, 20, 913", are reduced to the amino compounds of formula XXII in a solvent, with sulphuric acid conveniently being used, and in the presence of a metal, for example copper powder, at about 50°. Subsequently, treatment is carried out with a methanolic sodium azide solution according to usual methods. The resulting compound of formula XXIII is treated with triethylamine in a solvent, e.g. dichloromethane, under a protective gas atmosphere and with an alkylmalonyl chloride at 0°. After stirring at room temperature and subsequently under reflux conditions there are obtained compounds of formula VIa which can be converted according to the described process variant f) into the corresponding compounds of formula II in accordance with the invention.

Scheme 5

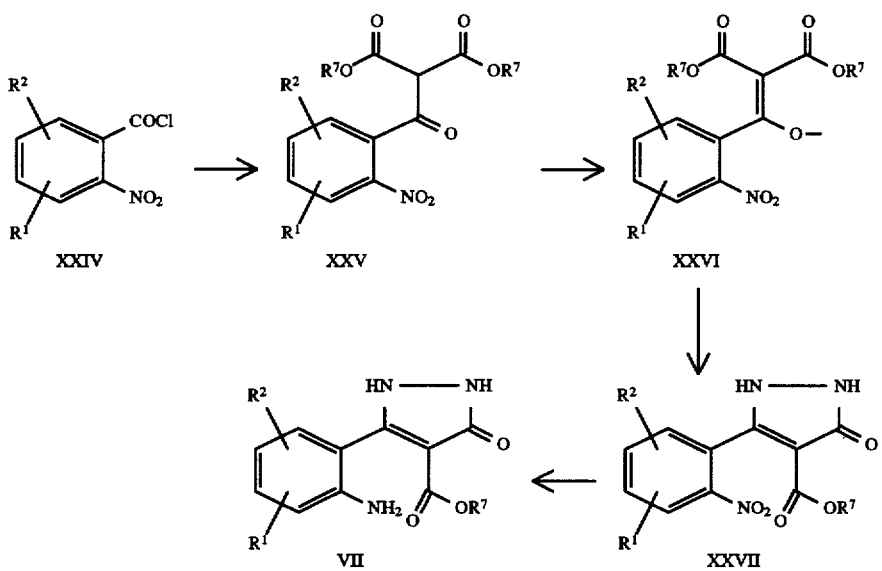

$R^1$, $R^2$ and $R^7$ have the significance given above.

Starting materials for the manufacture of compounds of general formula II in accordance with the invention in which X signifies —NH— can be obtained according to Scheme 5.

For the preparation of a compound of formula XXV, magnesium shavings are conveniently treated under a protective gas atmosphere with an ethanol/carbon tetrachloride mixture and subsequently a solution of a dialkyl malonate, ethanol and ether is added until the mixture boils slightly. After the dropwise addition of an appropriately substituted 2-nitrobenzoyl chloride in a suitable solvent mixture, for example in ether/tetrahydrofuran, the compounds of general formula XXV are obtained. These compounds are subsequently treated with a diazomethane solution to give the compounds of formula XXVI. By reacting an ethanolic solution of the compound XXVI with hydrazine hydrate there are obtained the compounds of formula XXVII. The hydrogenation of the nitro compound to the amino compound of formula VII is subsequently effected. This is usually effected using a metal catalyst, for example using a palladium catalyst, in a hydrogen stream at room temperature.

The compounds of formula VII are starting materials for the preparation of compounds of formula II in accordance with the invention according to process variant g).

Scheme 6

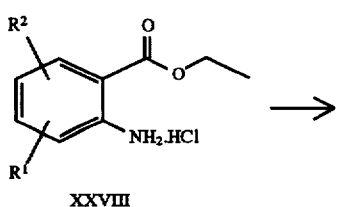

-continued
Scheme 6

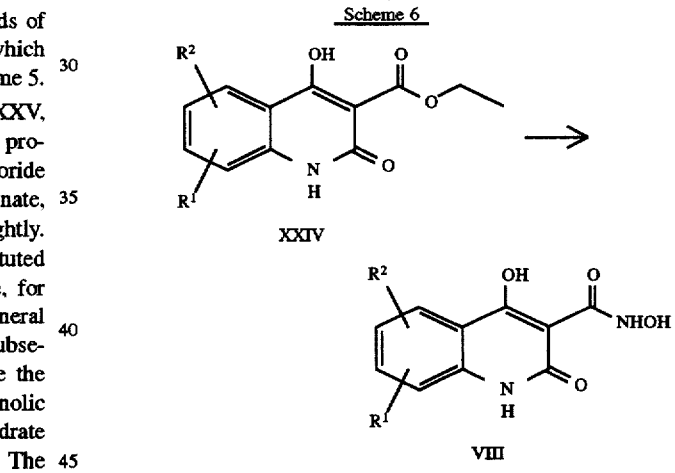

$R^1$ and $R^2$ have the significance given above.

Starting materials for the manufacture of compounds of formula II in accordance with the invention in which X signifies —O— can be prepared according to Scheme 6.

A solution of a compound of formula XXVIII, preferably in acetone, is treated with triethylamine and subsequently with methyl-malonyl chloride. After several hours reaction at room temperature the concentrated solution is treated with Na ethylate and the thus-obtained quinoline compound of formula XXIX is subsequently converted with trimethylsilylhydroxylamine into the compounds of formula VIII.

The resulting compounds are starting materials for the manufacture of compounds of formula II in accordance with the invention according to process variant h).

As mentioned earlier, the compounds of formulae Ia, Ib and II in accordance with the invention possess a pharmacological activity as non-competitive NMDA and/or AM PA/KA-R antagonists. On the basis of this activity the compounds of formulae Ia, Ib and II and their pharmaceutically usable salts can be used as neuroprotectives, especially for the treatment or prevention of ischemia, hypoglycaemia, hypoxia, cerebral vascular spasms, spasticity, trauma, hemorrhagia, infections (viral, bacterial, amoebic, prional), epileptic seizures, autoimmune diseases, withdrawal symptoms, Alzheimer's disease, Parkinson's disease, amyotrophic lateral sclerosis, Huntington's disease, intoxications, olivoponto-cerebellar atrophy, spinal cord injuries, schizophrenia, depressions, anxiety states, dependence, pains, autism and mental retardation.

The described substances competitively inhibit the binding of $^3$H-DCKA (3H-5,7-dichlorokynurenic acid) to the NMDA receptor and $^3$H-AMPA (DL-(3H)-amino-3-hydroxy-5-methyl-isoxazole-4-propionic acid) to the kainate/AMPA-receptor. $^3$H-DCKA and $^3$H-AMPA are specific ligands for the glycine binding site on the NMDA receptor and, respectively, the glutamate binding site on the kainate/AMPA receptor. The binding experiments were carried out analogously to described studies ($^3$H-DCKA binding: B. M. Baron et al., Eur. J. Pharmacol. 206 (1991) 149–154; $^3$H-AMPA binding: D. E. Murphy et al., Neurochem. Res. 12 (1987) 775–782).

Carefully washed membrane preparations from rat brain are used for the binding studies. The radioligands are used with concentrations of 20 nM $^3$H-DCKA and, respectively, 10 nM $^3$H-AMPA.

In order to determine the unspecific binding, the corresponding ligands with concentrations of 1 mM glycine and, respectively, 1 mM glutamate are added. Membrane-bound radioligand is separated from non-bound ligands by centrifugation (15 min, at 40 000 kg; $^3$H-DCKA) or filtration (combination of Whatmann GF/C and GF/B filters; $^3$H-AMPA).

The described substances are used in the binding experiments in different concentrations. The concentrations which inhibited 50% of the binding were determined on the basis of dosage-activity curves for the inhibition of the binding of the corresponding radioligands. These values (IC$_{50}$) are compiled in nM in Tables 1–3.

TABLE 1

Activity of the compounds of formula Ia on glycine NMDA-R and AMPA/KA-R

| Example No. | R$^1$ | R$^2$ | [$^3$H]-DCKA IC$_{50}$ (nM) | [$^3$H]-AMPA IC$_{50}$ (nM) |
|---|---|---|---|---|
| 3 | 8-Cl | H | 432 | 1750 |
| 6 | 8-F | H | 710 | 8160 |
| 8 | 8-Br | H | 322 | 1170 |
| 9 | 8-I | H | 189 | 1480 |
| 10 | 8-Cl | 9-F | 202 | 1250 |
| 11 | 8-Cl | 9-Cl | 31 | 660 |
| 12 | 8-Cl | 10-Cl | 79 | 620 |
| 14 | 8-CH$_3$ | 9-CH$_3$ | 132 | 2310 |
| 17 | 8-OCH$_3$ | H | 180 | 2370 |
| 21 | 8-NO$_2$ | H | 690 | 243 |
| 23 | 8-CF$_3$ | H | 379 | 1010 |
| 24 | 8-Cl | 9-NO$_2$ | 359 | 362 |
| 25 | 8-NO$_2$ | 9-Cl | 50 | 50 |
| 27 | 8-NO$_2$ | 9-F | 360 | 189 |
| 29 | 8-Cl | 9-NH$_2$ | 1320 | 8590 |
| 30 | 8-NO$_2$ | 9-N(CH$_3$)$_2$ | 342 | 47 |
| 32 | 8-NO$_2$ | 9-Pyrrolidin-1-yl | 3600 | 163 |
| 34 | 8-NO$_2$ | 9-Morpholin-4-yl | 8540 | 296 |
| 37 | 8-NO$_2$ | 9-NO$_2$ | 640 | 117 |
| 38 | 8-NO$_2$ | 9-Br | 68 | 71 |

TABLE 2

Activity of the compounds of formula Ib on glycine NMDA-R and AMPA/KA-R

| Example No. | R$^1$ | R$^2$ | [$^3$H]-DCKA IC$_{50}$ (nM) | [$^3$H]-AMPA IC$_{50}$ (nM) |
|---|---|---|---|---|
| 26 | 8-NO$_2$ | 9-Cl | 43 | 82 |
| 33 | 8-NO$_2$ | 9-Pyrrolidin-1-yl | 3060 | 336 |
| 36 | 8-NO$_2$ | 9-Imidazol-1-yl | 2560 | 16 |

TABLE 3

Activity of the compounds of formula II on glycine NMDA-R

| Example No. | X | R$_1$ | R$_2$ | [$^3$H]-DCKA IC$_{50}$ (nM) | [$^3$H]-AMPA IC$_{50}$ (nM) |
|---|---|---|---|---|---|
| 43 | —CH=N— | 8-Cl | H | 909 | >100 |
| 48 | —NH— | 7-Cl | H | 193 | 7310 |
| 49 | —NH— | 7-Cl | 8-Cl | 73 | 1370 |
| 55 | —O— | 7-NO$_2$ | H | 459 | 421 |
| 56 | —O— | 7-Cl | H | 266 | 20.000 |

The compounds of formulae Ia, Ib and II as well as their pharmaceutically usable salts can be used as medicaments, e.g. in the form of pharmaceutical preparations. The pharmaceutical preparations can be administered enterally such as orally, e.g. in the form of tablets, coated tablets, dragées, hard and soft gelatine capsules, solutions, emulsions or suspensions, nasally, e.g. in the form of nasal sprays, or rectally, e.g. in the form of suppositories. The administration can also be effected parenterally such as subcutaneously, intramuscularly or intravenously, e.g. in the form of injection solutions. For the production of tablets, coated tablets, dragées, and hard gelatine capsules, the compounds as well as their pharmaceutically usable salts can be processed with pharmaceutically inert, inorganic or organic excipients. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the production of solutions and syrups are e.g. water, polyols, saccharose, invert sugar, glucose etc. Suitable excipients for injection solutions are e.g. water, alcohols, polyols, glycerol, vegetable oils, etc. Suitable excipients for suppositories are e.g. natural or hardened oils, waxes, fats, semi-liquid or liquid polyols etc. The pharmaceutical preparations can, moreover, contain preservatives, solubilizers, viscosity-increasing substances, stabilizers, wetting agents, emulsifiers, sweeteners, colorants, flavorants, salts for varying the osmotic pressure, buffers, coating agents or antioxidants. They can also contain still other therapeutically valuable substances.

In accordance with the invention compounds of general formula I and II as well as their pharmaceutically acceptable salts can be used as neuroprotectives, especially in the treatment or prevention of ischemia, hypoglycaemia, hypoxia, cerebral vascular spasms, spasticity, trauma, hemorrhagia, infections (viral, bacterial, amoebic, prional), epileptic seizures, autoimmune diseases, withdrawal symptoms, Alzheimer's disease, Parkinson's disease, amyotrophic lateral sclerosis, Huntington's disease, intoxications, olivoponto-cerebellar atrophy, spinal cord injuries, schizophrenia, depressions, anxiety states, dependence, pains, autism and mental retardation. The dosage can vary within wide limits and will, of course, be fitted to the individual requirements in each particular case. In the case of oral administration the daily dosage lies in a range of about 50–500 mg, although the upper limit can also be exceeded when this is shown to be indicated.

The following Examples serve to illustrate the present invention in more detail. However, they are not intended to limit its scope in any manner. All temperatures are given in degrees Celsius.

Manufacture of the compounds of formulae Ia and Ib

EXAMPLE 1

2,3,5,6-Tetrahydro-1,2,4-triazolor[4,3-c]quinazoline-3,5-dione a) 1.2 g (7.4 mmol) of 1,2,3,4-tetrahydroquinazoline-2,4-dione were suspended in 10 ml (74 mmol) of phosphorus oxychloride and heated to 120° C. for 24 hrs. The reaction mixture was left to cool to room temperature and poured on to ice-water. The brown precipitate was dried and chromatographed over silica gel with methylene chloride as the eluent. There were obtained: 331 mg (22%) of 2,4-dichloroquinazoline as white crystals;

MS: me/e=198, 200 (M$^+$).

b) 281 mg (2.7 mmol) of ethyl carbazate were added to a solution of 360 mg (1.80 mmol) of 2,4-dichloroquinazoline in 5 ml of dimethyl sulphoxide. The reaction mixture was stirred at 80° C. for 4 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. There were obtained: 140 mg (31%) of ethyl 2-hydroxy-4-quinazolinecarbazate as white crystals;

MS: me/e=248 (M$^+$).

c) 150 mg (0.6 mmol) of ethyl 2-hydroxy-4-quinazolinecarbazate in 5 ml of dimethylformamide were heated at reflux for 2 hrs. The reaction mixture was cooled to room temperature and then poured on to ice-water. The precipitate was filtered off, washed with methanol and dried in a vacuum. There were obtained: 66 mg (54%) 2,3,5,6-tetrahydro-1,2,4-triazolo[4,3-c]-quinazoline-3,5-dione as white crystals;

MS: m/e=202 (M$^+$).

EXAMPLE 2

7-Chloro-2,3,5,6-tetrahydro-1,2,4-triazolo[4,3-c]quinazoline-3,5-dione a) A mixture of 5.0 g (0.03 mol) of 2-amino-3-chlorobenzoic acid and 3.5 g (0.06 mol) of urea was heated to 140° C. for 2 hrs. and at 180° C. for a further 24 hrs. The resulting brown mass was stirred with 50 ml of water and 50 ml of ethyl acetate, whereby a precipitate resulted. This was filtered off, dried in a vacuum and there were obtained beige crystals which were recrystallized from methanol. Yield: 3.5 g (63%) of 8-chloro-1,2,3,4-tetrahydroquinazoline-2,4-dione as white crystals; m.p. 224°–225° C.

b) 3.6 g (0.01 8 mol) of 8-chloro-1,2,3,4-tetrahydroquinazoline-2,4-dione were suspended in 16.8 ml (0.18 mol) of phosphorus oxychloride and boiled under reflux for 17 hrs. The reaction mixture was left to cool to room temperature and poured on to ice-water. The brown precipitate was extracted with dichloromethane, chromatographed over silica gel with dichloromethane as the eluent and recrystallized from diisopropyl ether. Yield: 2.26 g (53%) of 2,4,8-trichloro-quinazoline as yellow crystals; m.p. 155°–156° C.

c) 1.5 g (0.014 mol) of ethyl carbazate were added to a solution of 2.26 g (0.009 mol) of 2,4,8-trichloro-quinazoline in 95 ml of dimethyl sulphoxide. The reaction mixture was stirred at 70° C. for 2 hrs. and then poured on to ice-water. The yellow precipitate was filtered off, dried and recrystallized from methanol. Yield: 1.56 g (54%) of ethyl 2,8-dichloro-quinazoline-4-yl-carbazate as white crystals; m.p. 213°–215° C.

d) A solution of 1.56 g (0.0052 mol) of ethyl-2,8-dichloroquinazoline-4-yl-carbazate in 47 ml of dimethyl sulphoxide was heated to 95° C. for 6 hrs. The reaction mixture was left to cool to room temperature and poured on to ice-water. The white precipitate was filtered off and dried. Yield: 0.86 g (59%) of ethyl-8-chloro-2-hydroxy-quinazoline-4-yl-carbazate as white crystals; m.p. 348°–350° C.

e) 1.27 g (0.0045 mol) of ethyl-8-chloro-2-hydroxy-quinazoline-4-yl-carbazate in 75 ml of dimethylformamide were boiled under reflux for 2 hrs. The reaction mixture was cooled to room temperature and then poured on to ice-water. The precipitate was filtered off, dried in a vacuum and recrystallized from methanol/tetrahydrofuran. Yield: 0.66 g (62%) of 7-chloro-2,3,5,6-tetrahydro-1,2,4-triazolo[4,3-c]quinazoline-3,5-dione as yellowish crystals; m.p. 348°–350° C.

EXAMPLE 3

8-Chloro-2,3,5,6-tetrahydro-1,2,4-triazolo[4,3-c]quinazoline-3,5-dione a) A mixture of 18 g (0.105 mol) of 2-amino-4-chlorobenzoic acid and 12 g (0.20 mol) of urea was heated to 160° C. for 2 hrs. and at 180° C. for a further 2 hrs. The resulting brown mass was triturated with 200 ml of methanol, filtered off and dried in a vacuum. There were obtained: 12.2 g (59%) of 7-chloro-1,2,3,4-tetrahydro-quinazoline-2,4-dione as light brownish crystals;

MS: me/e=196 (M$^+$).

b) 10.5 g (0.053 mol) of 7-chloro-1,2,3,4-tetrahydro-quinazoline-2,4-dione were suspended in 35 ml (0.48 mol) of phosphorus oxychloride and heated to 120° C. for 24 hrs. The reaction mixture was left to cool to room temperature and poured on to ice-water. The brown precipitate was filtered off under suction, dried and chromatographed over silica gel with methylene chloride as the eluent.

There were obtained: 7.2 g (58%) of 2,4,7-trichloroquinazoline as yellow crystals;

MS: me/e=232, 234 (M$^+$).

c) 0.845 g (8.13 mmol) of ethyl carbazate was added to a solution of 0.95 g (4.07 mmol) of 2,4,7-trichloroquinazoline in 40 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. There was obtained 0.45 g (39%) of ethyl 7-chloro-2-hydroxy-4-quinazolinecarbazate as white crystals;

MS: me/e=282 (M$^+$).

d) 0.45 g (1.59 mmol) of ethyl 7-chloro-2-hydroxy-4-quinazolinecarbazate in 10 ml of dimethylformamide was heated at reflux for 2 hrs. The reaction mixture was cooled to room temperature and then poured on to ice-water. The precipitate was filtered off, washed with methanol and dried in a vacuum. There was obtained: 0.18 g (48%) of 8-chloro- 2,3,5,6-tetrahydro-1,2,4-triazolo[4,3-c]quinazoline-3,5-dione as white crystals;

MS: me/e=236 (M⁺).

EXAMPLE 4

9-Chloro-2,3,5,6-tetrahydro-1,2,4-triazolo[4,3-c]quinazoline-3,5-dione a) A mixture of 2.0 g (11.6 mmol) of 2-amino-5-chlorobenzoic acid and 3.48 g (58 mmol) of urea was heated to 160° C. for 2 hrs. and at 180° C. for a further 2 hrs. The resulting brown mass was triturated with 200 ml of methanol, filtered off and dried in a vacuum. There were obtained: 1.48 g (65%) of 6-chloro-1,2,3,4-tetrahydroquinazoline-2,4-dione as white crystals.

b) 1.4 g (7.13 mmol) of 6-chloro-1,2,3,4-tetrahydroquinazoline-2,4-dione were suspended in 7 ml (96 mmol) of phosphorus oxychloride and heated to 120° C. for 24 hrs. The reaction mixture was left to cool to room temperature and poured on to ice-water. The brown precipitate was filtered off, dried and chromatographed over silica gel with methylene chloride as the eluent. 1 g (60%) of 2,4,6-trichloroquinazoline was obtained as white crystals;

MS: me/e=232, 234 (M⁺).

c) 334 mg (3.2 mmol) of ethyl carbazate were added to a solution of 500 mg (2.1 mmol) of 2,4,6-trichloroquinazoline in 20 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 285 mg (47%) of ethyl 6-chloro-2-hydroxy-4-quinazolinecarbazate were obtained as yellow crystals;

MS: me/e=281 (M–H)⁺.

d) 0.16 g (0.68 mmol) of ethyl 6-chloro-2-hydroxy-4-quinazolinecarbazate in 15 ml of dimethylformamide was heated at reflux for 2 hrs. The reaction mixture was cooled to room temperature and then poured on to ice-water. The precipitate was filtered off, washed with methanol and dried in a vacuum. 35 mg (26%) of 9-chloro-2,3,5,6-tetrahydro-1,2,4-triazolo[4,3-c]quinazoline-3,5-dione were obtained as white crystals;

MS: me/e=236 (M⁺).

EXAMPLE 5

10-Chloro-2,3,5,6-1,2,4-triazolo[4,3-c]quinazoline-3,5-dione a) A mixture of 2.0 g (11 mmol) of 2-amino-6-chlorobenzoic acid and 1.4 g (23 mmol) of urea was heated to 160° C. for 2 hrs. and at 180° C. for a further 2 hrs. The resulting brown mass was triturated with 200 ml of methanol, filtered off and dried in a vacuum. 1.2 g (53%) of 5-chloro-1,2,3,4-tetrahydroquinazoline-2,4-dione were obtained as white crystals;

MS: me/e=196 (M⁺).

b) 0.5 g (2.54 mmol) of 5-chloro-1,2,3,4-tetrahydroquinazoline-2,4-dione was suspended in 7 ml (96 mmol) of phosphorus oxychloride and heated to 120° C. for 24 hrs. The reaction mixture was left to cool to room temperature and poured on to ice-water. The brown precipitate was filtered off, dried and chromatographed over silica gel with methylene chloride as the eluent. 260 mg (44%) of 2,4,5-trichloroquinazoline were obtained as white crystals;

MS: me/e=232, 234 (M⁺).

c) 134 mg (1.28 mmol) of ethyl carbazate were added to a solution of 200 mg. (0.85 mmol) of 2,4,5-trichloroquinazoline in 5 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 80 mg (37%) of ethyl 5-chloro-2-hydroxy-4-quinazolinecarbazate were obtained as white crystals;

MS: me/e=282 (M⁺).

d) 80 mg (0.28 mmol) of ethyl 5-chloro-2-hydroxy-4-quinazolinecarbazate in 5 ml of dimethylformamide were heated to reflux for 2 hrs. The reaction mixture was cooled to room temperature and then poured on to ice-water. The precipitate was filtered off, washed with methanol and dried in a vacuum. 38 mg (57%) of 10-chloro-2,3,5,6-tetrahydro-1,2,4-triazolo[4,3-c]quinazoline-3,5-dione were obtained as white crystals;

MS: me/e=236 (M⁺).

EXAMPLE 6

8-Fluoro-2,3,5,6-tetrahydro-1,2,4-triazolo[4,3-c]quinazoline-3,5-dione a) A mixture of 0.2 g (1.3 mmol) of 2-amino-4-fluorobenzoic acid and 1.16 g of urea (20 mmol) was heated to 160° C. for 2 hrs. and at 180° C. for a further 2 hrs. The resulting brown mass was triturated with 200 ml of methanol, filtered off and dried in a vacuum. There were obtained: 167 mg (70%) of 7-fluoro-1,2,3,4-tetrahydroquinazoline-2,4-dione as yellow crystals;

MS: me/e=180 (M⁺).

b) 164 mg (0.9 mmol) of 7-fluoro-1,2,3,4-tetrahydroquinazoline-2,4-dione were suspended in 3.5 ml (48 mmol) of phosphorus oxychloride and heated to 120° C. for 24 hrs. The reaction mixture was left to cool to room temperature and poured on to ice-water. The brown precipitate was filtered off under suction, dried and chromatographed over silica gel with methylene chloride as the eluent. 130 mg (67%) of 2,4-dichloro-7-fluoroquinazoline were obtained as orange coloured crystals;

MS: me/e=216, 218 (M⁺).

c) 562 mg (5.4 mmol) of ethyl carbazate were added to a solution of 780 mg (3.6 mmol) of 2,4-dichloro-7-fluoroquinazoline in 10 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 0.58 g (61%) of ethyl 7-fluoro-2-hydroxy-4-quinazolinecarbazate was obtained as light orange coloured crystals;

MS: me/e=266 (M⁺).

d) 30 mg (0.11 mmol) of 7-fluoro-2-hydroxy-4-quinazolinecarbazate in 2 ml of dimethylformamide were heated at reflux for 2 hrs. The reaction mixture was cooled to room temperature and then poured on to ice-water. The precipitate was filtered off, washed with methanol and dried in a vacuum. 10 mg (41%) of 8-fluoro-2,3,5,6-tetrahydro-1,2,4-triazolo[4,3-c]quinazoline-3,5-dione were obtained as white crystals;

MS: me/e=220 (M⁺).

EXAMPLE 7

9-Fluoro-2,3,5,6-tetrahydro-1,2,4-triazolo[4,3-c]quinazoline-3,5-dione

A mixture of 7.2 g (0.046 mol) of 2-amino-5-fluorobenzoic acid and 16.7 g (0.28 mol) of urea was heated to 180° C. for 3 hrs. The resulting brown mass was ground in a mortar, suspended in water overnight, filtered off, washed with water and subsequently with acetone and dried in a vacuum. Yield: 5.1 g (61%) of 6-fluoro-1,2,3,4-tetrahydroquinazoline-2,4-dione as brownish crystals; m.p. 335°–340° C. (dec.).

b) 5.1 g (0.028 mol) of 6-fluoro-1,2,3,4-tetrahydroquinazoline-2,4-dione were suspended in 39 ml (0.425 mol) of phosphorus oxychloride and heated to 105° C. for 18 hrs. The reaction mixture was left to cool to room temperature and poured on to ice-water. The brown precipitate was extracted with dichloromethane and chromatographed over silica gel with dichloromethane as the eluent. Yield: 5.0 g (81%) of 2,4-dichloro-6-fluoro-quinazoline as white crystals; m.p. 133°–136° C.

c) 3.43 g (0.033 mol) of ethyl carbazate were added to a solution of 5.5 g (0.025 mol) of 2,4-dichloro-6-fluoro-quinazoline in 220 ml of dimethyl sulphoxide. The reaction mixture was stirred at 70° C. for 2 hrs. and then poured on to ice-water. The precipitate was filtered off, dried and suspended in 200 ml of acetone. The crystals were filtered off and dried in a vacuum. Yield: 3.7 g (55%) of ethyl 6-fluoro-2-hydroxy-quinazolin-4-yl-carbazate as white crystals; m.p. >350° C.

MS: m/e (% base peak)=266 ($C_{11}H_{11}FN_4O_3^+$, 10), 220 (41), 180 (90), 137 (100), 109 (83), 82 (47).

d) 3.7 g (0.014 mol) of ethyl 6-fluoro-2-hydroxy-quinazolin-4-yl-carbazate in 75 ml of dimethylformamide were boiled under reflux for 2 hrs. The reaction mixture was cooled to room temperature and then poured on to ice-water. The precipitate was filtered off, washed with acetone and dried in a vacuum. Yield: 1.7 g (56%) of 9-fluoro-2,3,5,6-tetrahydro-1,2,4-triazolo[4,3-c]quinazoline-3,5-dione as yellowish crystals; m.p. >350° C.

MS: m/e (% base peak)=220 ($C_9H_5FN_4O_2^+$, 100), 163 (23), 136 (26), 135 (18), 121 (23), 108 (21), 43 (23).

EXAMPLE 8

8-Bromo-2,3,5,6-tetrahydro-1,2,4-triazolo[4,3-c]quinazoline-3,5-dione 63.8 mg (0.92 mmol) of sodium nitrite were added at 0° C. to a suspension of 210 mg (0.83 mmol) of 8-amino-2,3,5,6-tetrahydro-1,2,4-triazolo[4,3-c]quinazoline-3,5-dione hydrochloride in 5 ml of 48% hydrobromic acid. The mixture was stirred at 0° C. for 1 hr. and then 132 mg (0.99 mmol) of copper(I) bromide in 2 ml of water were added dropwise. After stirring at RT for 16 hrs. the precipitate was filtered off, washed with methanol and dried in a vacuum. 57 mg (24%) of 8-bromo-2,3,5,6-tetrahydro-1,2,4-triazolo[4,3-c]quinazoline-3,5-dione were obtained as yellowish crystals;

MS: m/e=280, 282 ($M^+$).

EXAMPLE 9

8-Iodo-2,3,5,6-tetrahydro-1,2,4-triazolo[4,3-c]quinazoline-3,5-dione 63.8 mg (0.92 mmol) of sodium nitrite were added at 0° C. to a suspension of 210 mg (0.83 mmol) of 8-amino-2,3,5,6-tetrahydro-1,2,4-triazolo[4,3-c]quinazoline-3,5-dione in 10 ml of acetic acid and 10 ml of sulphuric acid. The reaction mixture was stirred at 0° C. for 1 hr. Subsequently, 2.49 g (16.6 mmol) of sodium iodide in 10 ml of water were added dropwise and the mixture was stirred at RT for a further 1 hr. The precipitate was filtered off, the brown crystals were suspended in 10 ml of 5% sodium thiosulphate solution, filtered off and dried in a vacuum. 145 mg (53%) of 8-iodo-2,3,5,6-tetrahydro-1,2,4-triazolo[4,3-c]quinazoline-3,5-dione were obtained as brownish crystals;

MS: m/e =328 ($M^+$).

EXAMPLE 10

8-Chloro-9-fluoro-2,3,5,6-tetrahydro-1,2,4-triazolo[4,3-c]quinazoline-3,5-dione

A mixture of 8.9 g (0.047 mol) of 2-amino-4-chloro-5-fluoro-benzoic acid (R. Krishnan, S. A. Lang Jr., M. M. Siegel, *J. Het. Chem.* 1986, 23, 1801 ) and 17 g (0.28 mol) of urea was heated to 180° C. for 3 hrs. The resulting brown mass was ground in a mortar, suspended in water overnight, filtered off, washed with water and subsequently acetone and dried in a vacuum. Yield: 7.9 g (78%) of 7-chloro-6-fluoro-1,2,3,4-tetrahydroquinazoline-2,4-dione as brownish crystals; m.p. 320°–345° C. (dec.).

MS: m/e (% base peak)=214 ($C_8H_4ClFN_2O_2^+$, 76), 171 (100), 144 (52), 143(30), 116(16), 108(17), 81 (35).

b) 1.5 g (0.0070 mol) of 7-chloro-6-fluoro-1,2,3,4-tetrahydroquinazoline-2,4-dione were suspended in 9.6 ml (0.10 mol) of phosphorus oxychloride and heated to 105° C. for 84 hrs. The reaction mixture was left to cool to room temperature and poured on to ice-water. The brown precipitate was extracted with dichloromethane and chromatographed over silica gel with dichloromethane as the eluent. Yield: 1.45 g (82%) of 2,4,7-trichloro-6-fluoro-quinazoline as yellowish crystals; m.p. 90°–92° C.

c) 2.16 g (0.021 mol) of ethyl carbazate were added to a solution of 4.0 g (0.01 6 mol) of 2,4,7-trichloro-6-fluoroquinazoline in 160 ml of dimethyl sulphoxide. The reaction mixture was stirred at 70° C. for 2 hrs. and then poured on to ice-water. The precipitate was filtered off, rinsed with ethanol and dried in a vacuum. Yield: 1.6 g (34%) of ethyl 7-chloro-6-fluoro-2-hydroxy-quinazolin-4-yl-carbazate as yellow crystals; m.p. >350° C.

MS: m/e (% base peak)=300 ($C_{11}H_{10}ClFN_4O_3^+$, 18), 254 (100), 227 (14), 197 (20), 170 (27), 45 (22), 31 (50), 29 (50).

d) 1.6 g (0.0053 mol) of 7-chloro-6-fluoro-2-hydroxy-quinazolin-4-yl-carbazate in 30 ml of dimethylformamide were boiled under reflux for 2 hrs. The reaction mixture was cooled to room temperature and then poured on to ice-water. The precipitate was filtered off, washed with acetone and dried in a vacuum. Yield: 0.45 g (33%) of 8-chloro-9-fluoro-2,3,5,6-tetrahydro-1,2,4-triazolo[4,3-c]quinazoline-3,5-dione as yellowish crystals; m.p. >350° C.

MS: m/e (% base peak)=254 ($C_9H_4ClFN_4O_2^+$, 100), 197 (12), 170 (16), 155 (11), 142 (8), 58 (6).

EXAMPLE 11

8,9-Dichloro-2,3,5,6-tetrahydro-1,2,4-triazolo[4,3-c]quinazoline-3,5-dione a) A mixture of 0.3 g (1.5 mmol) of 2-amino-4,5-dichlorobenzoic acid and 875 mg (15 mmol) of urea was heated to 160° C. for 2 hrs. and at 180° C. for a further 2 hrs. The resulting brown mass was triturated with 200 ml of methanol, filtered off and dried in a vacuum. 230 mg (68%) of 5,6-dichloro-1,2,3,4-tetrahydroquinazoline-2,4-dione as white crystals;

MS: me/e=230, 232 (M⁺).

b) 200 mg (0.9 mmol) of 5,6-dichloro-1,2,3,4-tetrahydroquinazoline-2,4-dione were suspended in 3.5 ml (48 mmol) of phosphorus oxychloride and heated to 120° C. for 24 hrs. The reaction mixture was left to cool to room temperature and poured on to ice-water. The brown precipitate was filtered off under suction, dried and chromatographed over silica gel with methylene chloride as the eluent. 110 mg (47%) of 2,4,6,7-tetrachloroquinazoline were obtained as white crystals;

MS: me/e=268 (M⁺).

c) 53 mg (0.6 mmol) of ethyl carbazate were added to a solution of 100 mg (0.4 mmol) of 2,4,6,7-tetrachloroquinazoline in 2 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 55 mg (47%) of ethyl 6,7-dichloro-2-hydroxy-4-quinazolinecarbazate were obtained as white crystals;

MS: me/e=316 (M⁺).

d) 50 mg (0.11 mmol) of 6,7-dichloro-2-hydroxy-4-quinazolinecarbazate in 2 ml of dimethylformamide were heated to reflux for 2 hrs. The reaction mixture was cooled to room temperature and then poured on to ice-water. The precipitate was filtered off, washed with methanol and dried in a vacuum. 20 mg (46%) of 8,9-dichloro-2,3,5,6-tetrahydro-1,2,4-triazolo[4,3-c]quinazoline-3,5-dione were obtained as white crystals;

MS: me/e=270 (M⁺).

EXAMPLE 12

8,10-Dichloro-2,3,5,6-tetrahydro-1,2,4-triazolo[4,3-c] quinazoline-3,5-dione a) A mixture of 2 g (10 mmol) of 2-amino-4,6-dichlorobenzoic acid and 1.6 g (30 mmol) of urea was heated to 160° C. for 2 hrs. and at 180° C. for a further 2 hrs. The resulting brown mass was triturated with 200 ml of methanol, filtered off and dried in a vacuum. 880 mg (40%) of 5,7-dichloro-1,2,3,4-tetrahydroquinazoline-2,4-dione were obtained as beige crystals;

MS: me/e=230, 232 (M⁺).

b) 0.5 g (2 mmol) of 5,7-dichloro-1,2,3,4-tetrahydroquinazoline-2,4-dione was suspended in 3.5 ml (48 mmol) of phosphorus oxychloride and heated to 120° C. for 24 hrs. The reaction mixture was left to cool to room temperature and poured on to ice-water. The brown precipitate was dried and chromatographed over silica gel with methylene chloride. 276 mg (43%) of 2,4,5,7-tetrachloroquinazoline were obtained as white crystals;

MS: me/e=268 (M⁺).

c) 116 mg (1.1 mmol) of ethyl carbazate were added to a solution of 200 mg (0.75 mmol) of 2,4,5,7-tetrachloroquinazoline in 5 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. Yield: 90 mg (38%) of ethyl 5,7-dichloro-2-hydroxy-4-quinazolinecarbazate as white crystals;

MS: me/e=316 (M⁺).

d) 90 mg (0.28 mmol) of ethyl 5,7-dichloro-2-hydroxy-4-quinazolinecarbazate in 2 ml of dimethylformamide were heated at reflux for 2 hrs. The reaction mixture was cooled to room temperature and then poured on to ice-water. The precipitate was filtered off, washed with methanol and dried in a vacuum. Yield: 15 mg (20%) of 8,10-dichloro-2,3,5,6-tetrahydro-1,2,4-triazolo[4,3-c]quinazoline-3,5-dione as white crystals;

MS: me/e=270, 272 (M⁺).

EXAMPLE 13

7,8-Dimethyl-2,3,5,6-tetrahydro-1,2,4-triazolo[4,3-c] quinazoline-3,5-dione a) A mixture of 5.96 g (0.036 mol) of 2-amino-3,4-dimethylbenzoic acid and 4.33 g (0.072 mol) of urea was heated to 140° C. for 2 hrs. and at 180° C. for a further 2 hrs. The resulting brown mass was stirred with 100 ml of water and 100 ml of ethyl acetate, whereby a precipitate resulted. The precipitate was filtered off, dried in a vacuum and there were obtained light brownish crystals which were recrystallized from dimethylformamide/methanol. Yield: 4.26 g (62%) of 7,8-dimethyl-1,2,3,4-tetrahydroquinazoline-2,4-dione as beige crystals; m.p. 305°–307° C.

b) 7.96 g (0.042 mol) of 7,8-dimethyl-1,2,3,4-tetrahydroquinazoline-2,4-dione were suspended in 40 ml (0.43 mol) of phosphorus oxychloride and boiled under reflux for 16 hrs. The reaction mixture was left to cool to room temperature and poured on to ice-water. The brown precipitate was extracted with ethyl acetate, chromatographed over silica gel with dichloromethane as the eluent and recrystallized from ethyl acetate/n-hexane. Yield: 5.9 g (62%) of 2,4-dichloro-7,8-dimethyl-quinazoline as white crystals; m.p. 145°–146° C.

c) 5.40 g (0.051 mol) of ethyl carbazate were added to a solution of 5.83 g (0.025 mol) of 2,4-dichloro-7,8-dimethylquinazoline in 140 ml of dimethyl sulphoxide. The reaction mixture was stirred at 70° C. for 5 hrs. and then poured on to ice-water. The yellow precipitate was filtered off. The solution was concentrated and the residue was stirred in acetonitrile at room temperature overnight, whereby white crystals separated. The crystals were filtered off under suction and dried in a vacuum. Yield: 3.21 g (45%) of ethyl 2-hydroxy-7,8-dimethyl-quinazoline-4-yl-carbazate as white crystals; m.p. 370°–372° C.

d) 3.88 g (0.012 mol) of ethyl 2-hydroxy-7,8-dimethylquinazoline-4-yl-carbazate in 220 ml of dimethylformamide were boiled under reflux for 2 hrs. The reaction mixture was cooled to room temperature and then poured on to ice-water. The precipitate was filtered off and dried in a vacuum. There were obtained white crystals which were recrystallized from dimethylformamide. Yield: 1.62 g (50%) of 7,8-dimethyl-2,3,5,6-tetrahydro- 1,2,4-triazolo[4,3-c] quinazoline-3,5-dione as yellowish crystals; m.p. 380°–382° C.

EXAMPLE 14

8,9-Dimethyl-2,3,5,6-tetrahydro-1,2,4-triazolo[4,3-c] quinazoline-3,5-dione a) A mixture of 7.0 g (0.042 mol) of 2-amino-4,5-dimethylbenzioc acid and 5.07 g (0.084 mol) of urea was heated to 140° C. for 2 hrs. and at 180° C. for a further 2 hrs. The resulting brown mass was stirred with 50 ml of water and 50 ml of ethyl acetate, whereby a precipitate resulted. The precipitate was filtered off, dried in a vacuum and there were obtained light brownish crystals which were recrystallized from methanol/tetrahydrofuran. Yield: 4.5 g (56%) of 6,7-dimethyl-1,2,3,4-tetrahydroquinazoline-2,4-dione as beige crystals; m.p. 327°–329° C.

b) 4.5 g (0.023 mol) of 6,7-dimethyl-1,2,3,4-tetrahydroquinazoline-2,4-dione were suspended in 25 ml (0.27 mol) of phosphorus oxychloride and boiled under reflux for 16 hrs. The reaction mixture was left to cool to room temperature and poured on to ice-water. The brown precipitate was extracted with dichloromethane, chromatographed over silica gel with dichloromethane as the eluent and recrystallized from ethyl acetate/n-hexane. Yield: 2.48 g (46%) of 2,4-dichloro-6,7-dimethyl-quinazoline as white crystals; m.p. 140°–142° C.

c) 2.33 g (0.020 mol) of ethyl carbazate were added to a solution of 2.48 g (0.010 mol) of 2,4-dichloro-6,7-dimethyl-quinazoline in 60 ml of dimethyl sulphoxide. The reaction mixture was stirred at 70° C. for 5 hrs. and then poured on to ice-water. The yellow precipitate was filtered off, dried and recrystallized from dimethylformamide/methanol. Yield: 1.24 g (41%) of ethyl 2-hydroxy-6,7-dimethyl-quinazolin-4-yl-carbazate as white crystals; m.p. >350° C.

MS: me/e (% base peak)=276 ($C_{13}H_{16}N_4O_3^+$, 16), 230 (100), 203 (20), 174 (34), 146 (43), 131 (22), 31 (31).

d) 1.0 g (0.0030 mol) of ethyl 2-hydoxy-6,7-dimethyl-quinazolin-4-yl-carbazate in 57 ml of dimethylformamide was boiled under reflux for 2 hrs. The reaction mixture was cooled to room temperature and then poured on to ice-water. The precipitate was filtered off and dried in a vacuum. There were obtained white crystals which were recrystallized from dimethylformamide/methanol. Yield: 0.43 g (52%) of 8,9-dimethyl-2,3,5,6-tetrahydro-1,2,4-triazolo[4,3-c] quinazoline-3,5-dione as yellowish crystals; m.p. >350° C.

MS: me/e (% base peak)=230 ($C_{11}H_{10}N_4O_2^+$, 100), 215 (5), 186 (3.5), 173 (25), 146 (32),131 (14), 116 (13).

EXAMPLE 15

9,10-Dimethyl-2,3,5,6-tetrahydro-1,2,4-triazolo[4,3-c]quinazoline-3,5-dione a) A mixture of 11.8 g (0.070 mol) of 2-amino-5,6-dimethylbenzoic acid and 8.52 g (0.14 mol) of urea was heated to 140° C. for 2 hrs. and at 180° C. for a further 2 hrs. The resulting brown mass was stirred with 50 ml of water and 50 ml of ethyl acetate, whereby a precipitate resulted. The precipitate was filtered off and dried in a vacuum. Yield: 3.11 g (23%) of 5,6-dimethyl-1,2,3,4-tetrahydroquinazoline-2,4-dione as brown crystals; m.p. >350° C.

MS: me/e (% base peak)=190 ($C_{10}H_{10} N_2O_2^+$, 73), 147 (100), 120 (20), 118 (24), 104 (16), 91 (19).

b) 3.69 g (0.019 mol) of 5,6-dimethyl-1,2,3,4-tetrahydroquinazoline-2,4-dione were suspended in 17.7 ml (0.194 mol) of phosphorus oxychloride and boiled under reflux for 16 hrs. The reaction mixture was left to cool to room temperature and poured on to ice-water. The brown precipitate was extracted with dichloromethane, chromatographed over silica gel with dichloromethane as the eluent and recrystallized from ethyl acetate/n-hexane. Yield: 2.37 g (54%) of 2,4-dichloro-5,6-dimethyl-quinazoline as white crystals; m.p. 121°–123° C.

c) 2.2 g (0.020 mol) of ethyl carbazate were added to a solution of 2.37 g (0.010 mol) of 2,4-dichloro-5,6-dimethyl-quinazoline in 60 ml of dimethyl sulphoxide. The reaction mixture was stirred at 70° C for 5 hrs. and then poured on to ice-water. The yellow precipitate was filtered off and dried. Yield: 0.71 g (29%) of ethyl 5,6-dimethyl-2-hydroxy-quinazolin-4-yl- carbazate as yellowish crystals; m.p. 358°–360° C.

d) 0.67 g (0.0020 mol) of ethyl 5,6-dimethyl-2-hydroxy-quinazolin-4-yl-carbazate in 38 ml of dimethylformamide was boiled under reflux for 2 hrs. The reaction mixture was cooled to room temperature and then poured on to ice-water. The precipitate was filtered off and dried in a vacuum. There were obtained white crystals which were recrystallized from methanol/dimethylformamide. Yield: 0.41 g (74%) of 9,10-dimethyl-2,3,5,6-tetrahydro-1,2,4-triazolo[4,3-c] quinazoline-3,5-dione as yellowish crystals; m.p. >350° C.

MS: me/e (% base peak)=230 ($C_{11}H_{10}N_4O_2^+$, 100), 187 (27), 172 (42), 145 (25).

EXAMPLE 16

7-Methoxy-2,3,5,6-tetrahydro-1,2,4-triazolo[4,3-c]quinazoline-3,5-dione a) A mixture of 4.7 g (0.028 mol) of 2-amino-3-methoxybenzoic acid and 3.37 g (0.056 mol) of urea was heated to 140° C. for 2 hrs. and at 180° C. for a further 2 hrs. The resulting brown mass was stirred with 100 ml of water and 100 ml of ethyl acetate, whereby a precipitate resulted. The precipitate was filtered off and dried in a vacuum. Yield: 3.28 g (61%) of 8-methoxy- 1,2,3,4-tetrahydroquinazoline-2,4-dione as beige crystals; m.p. 266°–268° C.

b) 3.28 g (0.017 mol) of 8-methoxy-1,2,3,4-tetrahydroquinazoline-2,4-dione were suspended in 15.6 ml (0.17 mol) of phosphorus oxychloride and boiled under reflux for 16 hrs. The reaction mixture was left to cool to room temperature and poured on to ice-water. The brown precipitate was extracted with dichloromethane, chromatographed over silica gel with dichloromethane as the eluent and recrystallized from diisopropyl ether. Yield: 2.38 g (61%) of 2,4-dichloro-8-methoxy-quinazoline as white crystals; m.p. 161°–162° C.

c) 1.59 g (0.015 mol) of ethyl carbazate were added to a solution of 2.38 g (0.010 mol) of 2,4-dichloro-8-methoxyquianazoline in 60 ml of dimethyl sulphoxide. The reaction mixture was stirred at 70° C. for 3 hrs. and then poured on to ice-water. The brown precipitate was filtered off. The yellow solution was concentrated and the residue was stirred overnight in an acetonitrile/ethanol 4:1 mixture at room temperature, whereby a white precipitate separated. The precipitate was filtered off under suction, dried in a vacuum and recrystallized from methanol/ether. Yield: 1.06 g (61%) of ethyl 2-hydroxy-8-methoxy-quinazolin-4-yl-carbazate as white crystals; m.p. 314°–316° C.

d) 1.02 g (0.0036 mol) of ethyl 2-hydroxy-8-methoxy-quinazolin-4-yl-carbazate in 65 ml of dimethylformamide were boiled under reflux for 2 hrs. The reaction mixture was cooled to room temperature and then poured on to ice-water. The precipitate was filtered off and dried in a vacuum. There were obtained white crystals which were recrystallized from methanol. Yield: 0.52 g (61%) of 7-methoxy-2,3,5,6-tetrahydro-1,2,4-triazolo[4,3-c]quinazoline-3,5-dione as yellowish crystals; m.p. 308°–310° C.

EXAMPLE 17

8-Methoxy-2,3,5,6-tetrahydro-1,2,4-triazolo[4,3-c]quinazoline-3,5-dione a) A solution of 1.0 g (0.015 mol) of sodium cyanate in 10 ml of water was added dropwise at 70° C. within 10 minutes to a suspension of 1.7 g (0.010 mol) of 2-amino-4-methoxybenzoic acid in 17 ml of acetic acid. After stirring for a further 10 minutes the white suspension obtained was cooled to room temperature, diluted with water and subsequently suction filtered. The crystals obtained were boiled under reflux for 30 minutes in 15 ml of 37 per cent aqueous hydrochloric acid, cooled, diluted with 75 ml of water, filtered off under suction, rinsed with water and dried in a vacuum. Yield: 0.73 g (37%) of 7-methoxy-1,2,3,4-tetrahydroquinazoline-2,4-dione as white crystals; m.p. 320°–323° C.

b) 10 g (0.052 mol) of 7-methoxy-1,2,3,4-tetrahydroquinazoline-2,4-dione were suspended in 72 ml (0.78 mol) of phosphorus oxychloride and heated to 105° C. for 4 hrs. The mixture was left to cool to room temperature, treated with toluene, cautiously poured on to ice-water and filtered over Dicalite. The aqueous phase was extracted with ethyl acetate, the organic phases were combined and concentrated and the residue was chromatographed over silica gel with dichloromethane as the eluent. Yield: 10.8 g (91%) of 2,4-dichloro-7-methoxy-quinazoline as white crystals; m.p. 123°–124° C.

c) 2.72 g (0.026 mol) of ethyl carbazate were added to a solution of 4.0 g (0.0175 mol) of 2,4-dichloro-7-methoxy-quinazoline in 160 ml of dimethyl sulphoxide. The reaction mixture was stirred at 70° C. for 2 hrs. and then poured on to ice-water. The precipitate was filtered off, the solution was concentrated and the residue was suspended in methanol. The suspension was suction filtered, washed with a small amount of methanol and dried in a vacuum. Yield: 1.65 g (34%) of ethyl 2-hydroxy- 7-methoxy-quinazolin-4-yl-carbazate as off-white crystals; m.p. 330°–332° C.

d) 1.65 g (0.0059 mol) of ethyl 2-hydroxy-7-methoxy-quainazolin-4-yl-carbazate in 30 ml of dimethylformamide were boiled under reflux for 2 hrs. The reaction mixture was cooled to room temperature and then poured on to ice-water. The precipitate was filtered off, washed with methanol and dried in a vacuum. There were obtained white crystals which were recrystallized from methanol. Yield: 0.58 g (42%) of 8-methoxy-2,3,5,6-tetrahydro-1,2,4-triazolo[4,3-c] quinazoline-3,5-dione as white crystals; m.p. 344°–346° C.

EXAMPLE 18

9-Methoxy-2,3,5,6-tetrahydro-1,2,4-triazolo[4,3-c] quinazoline-3,5-dione a) 12.5 g (0.075 mol) of 2-amino-5-methoxy-benzoic acid were dissolved in 60 ml of 2N hydrochloric acid, whereby after 10 sec. a mass which could not be stirred formed; this was placed in suspension after dilution with 120 ml of water. Then, a solution of 6.8 g (0.105 mol) of sodium cyanate in 70 ml of water was added dropwise at room temperature within 10 minutes. After stirring for a further 16 hrs. the suspension obtained was suction filtered, washed with water and subsequently with ether and dried in a vacuum. The crystals obtained were boiled under reflux for 1 hr. in 75 ml of 37 per cent aqueous hydrochloric acid, cooled, diluted with 300 ml of water, filtered off under suction, washed with water and dried in a vacuum. Yield: 8.6 g (60%) of 5-methoxy-1,2,3,4-tetrahydroquinazoline-2,4-dione as beige crystals; m.p. 330°–340° C.

b) 7.3 g (0.038 mol) of 5-methoxy-1,2,3,4-tetrahydroquinazoline-2,4-dione were suspended in 52 ml (0.57 mol) of phosphorus oxychloride and heated to 105° C. for 18 hrs. The mixture was left to cool to room temperature, treated with toluene, cautiously poured on to ice-water and filtered over Dicalite. The aqueous phase was extracted with ethyl acetate, the organic phases were combined and concentrated and the residue was chromatographed over silica gel with dichloromethane as the eluent. Yield: 8.0 g (92%) of 2,4-dichloro-6-methoxy-quinazoline as yellowish crystals; m.p. 175°–177° C.

c) 4.8 g (0.046 mol) of ethyl carbazate were added to a solution of 8.0 g (0.035 mol) of 2,4-dichloro-6-methoxy-quinazoline in 320 ml of dimethyl sulphoxide. The reaction mixture was stirred at 70° C. for 2 hrs. and then poured on to ice-water. The precipitate was filtered off under suction, washed with water and suspended in 50 ml of methanol. The suspension was suction filtered, rinsed with a small amount of methanol and dried in a vacuum. Yield: 3.0 g (31%) of ethyl 2-hydroxy-6-methoxy-quinazolin-4-yl-carbazate as white crystals; m.p. >350° C.

MS: me/e (% base peak)=278 ($C_{12}H_{14}N_4O_4^+$, 7.5), 232 (100), 217 (19), 205 (7.5), 191 (9), 176 (30), 148 (22), 133 (26), 45 (25), 31 (43), 29(38).

d) 3.0 g (0.011 mol) of ethyl 2-hydroxy-6-methoxy-quinazoline-4-yl-carbazate in 70 ml of dimethylformamide were boiled under reflux for 2 hrs. The reaction mixture was cooled to room temperature and then poured on to ice-water. The precipitate was filtered off, washed with methanol and dried in a vacuum. There were obtained white crystals which were recrystallized from methanol/acetone. Yield: 1.16 g (46%) of 9-methoxy-2,3,5,6-tetrahydro-1,2,4-triazolo[4,3-c] quinazoline-3,5-dione as beige crystals; m.p. >350° C.

MS: me/e (% base peak)=232 ($C_{10}H_8N_4O_3^+$, 100), 217 (26), 190 (6.5), 176 (36), 161 (14), 148 (42), 133 (64).

EXAMPLE 19

10-Methoxy-2,3,5,6-tetrahydro-1,2,4-triazolo[4,3-c] quinazoline-3,5-dione a) A solution of 16.6 g (0.255 mol) of sodium cyanate in 170 ml of water was added dropwise at room temperature within 40 minutes to a solution of 14.2 g (0.085 mol) of 2-amino-6-methoxy-benzoic acid in 150 ml of 2N hydrochloric acid. After 2 hrs. a further 100 ml of 2N hydrochloric acid and subsequently 8.3 g (0.13 mol) of sodium cyanate in 85 ml of water were added dropwise. After stirring for a further 67 hrs. the white suspension obtained was suction filtered, washed with water and subsequently ethyl acetate and dried in a vacuum. The crystals obtained were boiled under reflux for 30 minutes in 80 ml of 37 percent aqueous hydrochloric acid, cooled, diluted with 500 ml of water, filtered off under suction, rinsed with water and subsequently with acetone and dried in a vacuum. Yield: 8.35 g (51%) of 5-methoxy-1,2,3,4-tetrahydroquinazoline-2,4-dione as white crystals; m.p. >350° C.

MS: me/e (% base peak)=192 ($C_9H_8N_2O_3^+$, 74), 174 (11 ), 163 (100), 149 (27), 146 (36), 122 (48), 119 (57), 107 (65).

b) 9.7 g (0.50 mol) of 5-methoxy-1,2,3,4-tetrahydroquinazoline-2,4-dione were suspended in 70 ml (0.76 mol) of phosphorus oxychloride and heated to 105° C. for 20 hrs. The mixture was left to cool to room temperature, treated with toluene, cautiously poured on to ice-water and filtered over Dicalite. The aqueous phase was extracted with ethyl acetate, the organic phases were combined and concentrated and the residue was chromatographed over silica gel with dichloromethane as the eluent. Yield: 8.9 g (77%) of 2,4-dichloro-5-methoxy-quinazoline as white crystals; m.p. 169°–170° C.

c) 3.0 g (0.29 mol) of ethyl carbazate were added to a solution of 5.0 g (0.22 mol) of 2,4-dichloro-5-methoxy-quinazoline in 200 ml of dimethyl sulphoxide. The reaction mixture was stirred at 70° C. for 2 hrs. and then poured on to ice-water. The precipitate was filtered off, the solution was concentrated and the residue was suspended in an acetonitrile/ethanol 7:3 mixture. The residue was filtered off under suction and the cake was recrystallized from hot methanol. Yield: 2.0 g (33%) of ethyl 2-hydroxy-5-methoxy-quinazolin-4-yl-carbazate as yellowish crystals; m.p. >350° C.

MS: m/e (% base peak)=278 ($C_{12}H_{14}N_4O_4^+$, 13), 232 (100), 203 (29), 190 (45), 175 (26), 161 (40), 145 (19), 118 (34), 45 (40), 31, (84).

d) 2.4 g (0.0086 mol) of ethyl 2-hydroxy-5-methoxy-quinazolin-4-yl-carbazate in 50 ml of dimethylformamide were boiled under reflux for 3 hrs. The reaction mixture was cooled to room temperature and then poured on to ice-water. The precipitate was filtered off, washed with methanol and dried in a vacuum. There were obtained white crystals which were recrystallized from dimethylformamide. Yield: 0.32 g (16%) of 10-methoxy-2,3,5,6-tetrahydro-1,2,4-triazolo[4,3-c]quinazoline-3,5-dione as white crystals; m.p. >350° C.

MS: m/e (% base peak)=232 ($C_{10}H_8N_4O_3^+$, 100), 203 (34), 161 (43), 145 (23), 118 (29).

EXAMPLE 20

7-Nitro-2,3,5,6-tetrahydro-1,2,4-triazolo[4,3-c]quinazoline-3,5-dione a) A mixture of 10.7 g (0.059 mol) of 2-amino-3-nitrobenzoic acid and 21.6 g (0.35 mol) of urea was heated to 180° C. for 5 hrs. The resulting brown mass was ground in a mortar, suspended in water overnight, filtered off, washed with water and subsequently with acetone and dried in a vacuum. Yield: 7.70 g (63%) of 8-nitro-1,2,3,4-tetrahydroquinazoline-2,4-dione as brownish crystals; m.p. 277°–276° C. (dec.).

b) 7.70 g (0.037 mol) of 8-nitro-1,2,3,4-tetrahydroquinazoline-2,4-dione were suspended in 51 ml (0.56 mol) of phosphorus oxychloride and heated to 105° C. for 40 hrs. The suspension was left to cool to room temperature, treated with 250 ml of toluene, filtered off under suction and cautiously poured into 0.5 l of water. The aqueous phase was extracted with ethyl acetate, the organic phases were combined and concentrated and the residue was chromatographed over silica gel with dichloromethane. Yield: 4.50 g (50%) of 2,4-dichloro-8-nitro-quinazoline as yellow crystals; m.p. 155°–157° C.

c) 2.44 g (0.023 mol) of ethyl carbazate were added to a solution of 4.40 g (0.018 mol) of 2,4-dichloro-8-nitro-quinazoline in 160 ml of dimethyl sulphoxide. The reaction mixture was stirred at 70° C. for 2 hrs. and then poured on to ice-water. The precipitate was filtered off and dried. The solution was concentrated totally; the residue was taken up in methanol, the precipitate was filtered off under suction and combined with the first precipitate. Yield: 1.54 g (29%) of ethyl 2-hydroxy-8-nitro-quinazolin-4-yl-carbazate as orange coloured crystals; m.p. >350° C.

MS: m/e (% base peak)=293 ($C_{11}H_{11}N_5O_5^+$, 25), 221 (18), 220 (17), 174 (30), 146 (19), 29 (100).

d) 2.20 g (0.0075 mol) of ethyl 2-hydroxy-8-nitro-quinazolin-4-yl-carbazate in 50 ml of dimethylformamide were boiled under reflux for 2 hrs. The reaction mixture was cooled to room temperature and then poured on to ice-water. The precipitate was filtered off, suspended in methanol overnight, filtered off under suction and dried in a vacuum. There were obtained white crystals which were recrystallized from methanol. Yield: 1.1 g (59%) of 7-nitro-2,3,5,6-tetrahydro-1,2,4-triazolo[4,3-c]quinazoline-3,5-dione as yellow crystals; m.p. >350° C.

MS: m/e (% base peak)=247 ($C_9H_5N_5O_4^+$, 100), 207 (9), 174 (9), 144 (12), 130 (14), 117 (19), 90 (14).

EXAMPLE 21

8-Nitro-2,3,5,6-tetrahydro-1,2,4-triazolo[4,3-c]quinazoline-3,5-dione a) A mixture of 5 g (0.027 mol) of 2-amino-4-nitrobenzoic acid and 16.5 g (0.27 mol) of urea was heated to 160° C. for 2 hrs. and at 180° C. for a further 2 hrs. The resulting brown mass was triturated with 200 ml of methanol, filtered off and dried in a vacuum. 4.8 g (80%) of 7-nitro-1,2,3,4-tetrahydro-quinazoline-2,4-dione were obtained as a white solid;

MS: m/e=207 (M$^+$).

b) 18.6 ml (0.204 mol) of phosphorus oxychloride were added to a solution of 3.5 g (0.01 7 mol) of 7-nitro-1,2,3,4-tetrahydroquinazoline-2,4-dione and 6.5 ml (0.051 mol) of collidine in 60 ml of acetonitrile and the mixture was subsequently heated at reflux for 4 hrs. The solvent was removed on a rotary evaporator and the residue was partitioned between 300 ml of water and 300 ml of ethyl acetate. The organic phase was washed with 200 ml of saturated NaHCO$_3$ solution and 2× with 200 ml of saturated sodium chloride solution and finally dried over sodium sulphate. After filtration and concentration the residue was chromatographed over Florisil with methylene chloride as the eluent. 2.46 g (60%) of 2,4-dichloro-7-nitroquinazoline were obtained as yellow crystals;

MS: m/e=243, 245 (M$^+$).

c) 1.574 g (0.015 mol) of ethyl carbazate were added to a solution of 2.45 g (0.01 mol) of 2,4-dichloro-7-nitroquinazoline in 100 ml of dimethyl sulphoxide. The reaction mixture was stirred at RT for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 1.77 g (60%) of ethyl 7-nitro-2-hydroxy-4-quinazolinecarbazate were obtained as yellow crystals.

d) 1.7 g (5.4 mmol) of ethyl 7-nitro-2-hydroxy-4-quinazolinecarbazate in 20 ml of dimethylformamide were heated to reflux for 2 hrs. The reaction mixture was cooled to room temperature and then poured on to ice-water. The precipitate was filtered off, washed with methanol and dried in a vacuum. 1.15 g (77%) of 8-nitro-2,3,5,6-tetrahydro-1,2,4-triazolo[4,3-c]quinazoline-3,5-dione were obtained as yellow crystals;

MS: m/e=247 (M$^+$).

EXAMPLE 22

9-Nitro-2,3,5,6-tetrahydro-1,2,4-triazolo[4,3-c]quinazoline-3,5-dione a) A mixture of 2.0 g (10 mmol) of 2-amino-5-nitrobenzoic acid and 6.6 g (110 mmol) of urea was heated to 160° C. for 2 hrs. and at 180° C. for a further 2 hrs. The resulting brown mass was triturated with 200 ml of methanol, filtered off and dried in a vacuum. 2 g (78%) of 5-nitro-1,2,3,4-tetrahydroquinazoline-2,4-dione were obtained as pale brown crystals;

MS: m/e=207 (M$^+$).

b) 1 g (5 mmol) of 5-nitro-1,2,3,4-tetrahydroquinazoline-2,4-dione were suspended in 7 ml (96 mmol) of phosphorus oxychloride and heated to 120° C. for 24 hrs. The reaction mixture was left to cool to room temperature and poured on to ice-water. The brown precipitate was filtered off, dried and chromatographed over silica gel with methylene chloride as the eluent. 754 mg (63%) of 2,4-dichloro-6-nitroquinazoline were obtained as white crystals;

MS: m/e=243, 245 (M⁺).

c) 480 mg (4.6 mmol) of ethyl carbazate were added to a solution of 750 mg (3.1 mmol) of 2,4-dichloro-6-nitroquinazoline in 15 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C for 2 hrs. The mixture was left to cool to room temperature, the crystals were filtered off and dried in a vacuum. Yield: 640 mg (71%) of ethyl 2-hydroxy-7-nitro-4-quinazolinecarbazate as yellow crystals;

MS: m/e=293 (M⁺).

d) 620 mg (2.1 mmol) of ethyl 2-hydroxy-7-nitro-4-quinazolinecarbazate in 15 ml of dimethylformamide were heated at reflux for 2 hrs. The reaction mixture was cooled to room temperature and then poured on to ice-water. The precipitate was filtered off, washed with methanol and dried in a vacuum. 460 mg (88%) of 9-nitro-2,3,5,6-tetrahydro-1,2,4-triazolo[4,3-c]quinazoline-3,5-dione were obtained as yellow crystals;

MS: m/e=247 (M⁺).

EXAMPLE 23

8-Trifluoromethyl-2,3,5,6-tetrahydro-1,2,4-triazolo[4,3-c]quinazoline-3,5-dione a) A mixture of 1.0 g (0.005 mol) of 2-amino-4-trifluoromethylbenzoic acid and 2.64 g (0.044 mol) of urea was heated to 160° C. for 2 hrs. and at 180° C. for a further 2 hrs. The resulting brown mass was triturated with 200 ml of methanol, filtered off and dried in a vacuum. 0.7 g (62.5%) of 7-trifluoromethyl-1,2,3,4-tetrahydroquinazoline-1,4-dione was obtained as light brownish crystals;

MS: m/e=230 (M⁺).

b) 200 mg (0.87 mmol) of 7-trifluoromethyl-1,2,3,4-tetrahydroquinazoline-1,4-dione were suspended in 3.5 ml (48 mmol) of phosphorus oxychloride and heated to 120° C. for 24 hrs. The reaction mixture was left to cool to room temperature and poured on to ice-water. The brown precipitate was filtered off under suction, dried and chromatographed over silica gel with methylene chloride as the eluent. 142 mg (58%) of 2,4-dichloro-7-trifluoromethylquinazoline were obtained as rose coloured crystals;

MS: m/e=266, 286 (M⁺).

c) 500 mg (4.8 mmol) of ethyl carbazate were added to a solution of 630 mg (2.37 mmol) of 2,4-dichloro-7-trifluoromethylquinazoline in 20 ml of dimethyl sulphoxide. The reaction mixture was stirred at 70° C. for 2 hrs. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. 0.46 g (61%) of ethyl 2-hydroxy-7-trifluoromethyl-4-quinazolinecarbazate was obtained as white crystals;

MS: m/e=316 (M⁺).

d) 0.35 g (1.11 mmol) of ethyl 2-hydroxy-7-trifluoromethyl-4-quinazolinecarbazate in 10 ml of dimethylformamide was heated to reflux for 2 hrs. The reaction mixture was cooled to room temperature and then poured on to ice-water. The precipitate was filtered off, washed with methanol and dried in a vacuum. 0.11 g (38%) of 8-trifluoromethyl-2,3,5,6-tetrahydro-1,2,4-triazolo[4,3-c]quinazoline-3,5-dione was obtained as white crystals;

MS: m/e=270 (M⁺).

EXAMPLE 24

8-Chloro-9-nitro-2,3,5,6-tetrahydro-1,2,4-triazolo[4,3-c]quinazoline-3,5-dione a) 20 g (101.7 mmol) 7-chloro-1,2,3,4-tetrahydroquinazoline-2,4-dione were dissolved in 100 ml of conc. sulphuric acid and treated with 7 ml of conc. nitric acid. The mixture was heated to 100° C. for 10 min. After cooling the reaction mixture was poured on to ice-water. The precipitate was filtered off, dried in a high vacuum and recrystallized from acetic acid. 13.3 g (54%) of 7-chloro-6-nitro-1,2,3,4-tetrahydroquinazoline-2,4-dione were obtained as beige crystals;

MS: m/e=241 (M⁺).

b) 2.2 g (9.1 mmol) of 7-chloro-6-nitro-1,2,3,4-tetrahydroquinazoline-2,4-dione were suspended in 15 ml of acetonitrile and heated at reflux for 3 hrs. with 10 ml (110 mmol) of phosphorus oxychloride and 3.6 ml (27.3 mmol) of collidine. After removing the solvent the residue was suspended in methylene chloride, filtered over Florisil and dried in a vacuum. 1.4 g (55%) of 6-nitro-2,4,7-trichloroquinazoline were obtained as white crystals;

MS: m/e=277, 279 (M⁺).

c) 0.54 g (5.2 mmol) of ethyl carbazate was added to a solution of 1.0 g (3.6 mmol) of 6-nitro-2,4,7-trichloroquinazoline in 25 ml of dimethyl sulphoxide. The reaction mixture was stirred at room temperature for 2 hrs. and subsequently at 70° C. for 1 hr. and then poured on to ice-water. The brown precipitate was filtered off and dried. The brown crystals were suspended in 20 ml of n-butanol and the suspension was heated to 90° C. for 2 hrs. The mixture was left to cool to room temperature, the crystals were filtered off and dried in a vacuum. There were obtained: 660 mg (56%) of ethyl 7-chloro-6-nitro-2-hydroxy-4-quinazolinecarbazate as yellow crystals;

MS: m/e=327 (M⁺).

d) 550 mg (1.68 mmol) of ethyl 7-chloro-6-nitro-2-hydroxy-4-quinazolinecarbazate in 5 ml of dimethylformamide were heated to reflux for 2 hrs. The reaction mixture was cooled to room temperature and then poured on to ice-water. The precipitate was filtered off, washed with methanol and dried in a vacuum. 327 mg (69%) of 8-chloro-9-nitro-2,3,5,6-tetrahydro-1,2,4-triazolo[4,3-c]quinazoline-3,5-dione were obtained as orange coloured crystals;

MS: m/e=281 (M⁺).

EXAMPLE 25

9-Chloro-8-nitro-2,3,5,6-tetrahydro-1,2,4-triazolo[4,3-c]quinazoline-3,5-dione a) A mixture of 6.0 g (27.7 mmol) of 2-amino-5-chloro-4-nitrobenzoic acid and 10.0 g (0.166 mol) of urea was heated at 180° C. for 2.5 hrs. The resulting brown mass was boiled with 200 ml of water. Subsequently, it was filtered off, washed with water and with acetone and dried in a vacuum. 4.35 g (65%) of 2,4-dioxo-6-chloro-7-nitro-1,2,3,4-tetrahydroquinoline were obtained as a dark brown powder;

MS: m/e=243 (M⁺), 241 (M⁺).

b) 4.35 g (18.0 mmol) of 2,4-dioxo-6-chloro-7-nitro-1,2,3,4-tetrahydroquinazoline were suspended in 40 ml of phosphorus oxychloride and heated to 140° C. for 48 hrs. The reaction mixture was left to cool to room temperature and poured on to ice-water. Subsequently, the mixture was extracted with methylene chloride and the organic phase was dried over magnesium sulphate, filtered and concentrated.

The residue was dried and chromatographed over silica gel with methylene chloride as the eluent. 2.535 g (50%) of 2,4,6-trichloro-7-nitroquinazoline were obtained as yellow crystals;

MS: me/e=277 (M⁺), 279 (M⁺), 281 (M⁺).

c) 1.23 g (11.8 mmol) of ethyl carbazate were added to a solution of 2.535 g (9.1 mmol) of 2,4,6-trichloro-7-nitroquinazoline in 40 ml of dry dimethyl sulphoxide. After one hour the mixture was poured on to ice-water. The yellow precipitate was filtered off, dried and chromatographed over silica gel with ethyl acetate-hexane (1:1) as the eluent. 2.61 g (83%) of ethyl 2,6-dichloro-7-nitro-4-quinazolinecarbazate were obtained as yellow crystals;

MS: me/e=345 (M⁺), 347 (M⁺).

d) A solution of 2.6 g (7.5 mmol) of ethyl 2,6-dichloro-7-nitro-4-quinazolinecarbazate and 50 ml of dry dimethyl sulphoxide was heated to 100° C. for 1.5 hrs. Subsequently, the mixture was poured on to ice and the yellow precipitate was filtered off and dried. 2.35 g (95%) of ethyl 6-chloro-7-nitro-2-hydroxy-4-quinazolinecarbazate were obtained as yellow crystals;

MS: me/e=327 (M⁺), 329 (M⁺).

e) 2.33 g (7.11 mmol) of ethyl 6-chloro-7-nitro-2-hydroxy-4-quinazolinecarbazate in 100 ml of dimethylformamide were heated at reflux for 1.5 hrs. The reaction mixture was cooled to room temperature and the solvent was removed on a rotary evaporator. The residue was triturated with 50 ml of acetone and the pale yellow precipitate was filtered off, washed with a small amount of acetone and dried in a vacuum. 1.284 g (64%) of 9-chloro-8-nitro-2,3,5,6-tetrahydro-1,2,4-triazolo[4,3-c]quinazoline-3,5-dione were obtained as beige crystals;

MS: me/e=281 (M⁺), 283 (M⁺).

EXAMPLE 26

9-Chloro-8-nitro-1-yl-2,3,5,6-tetrahydro-[1,2,4]triazolo[1,5-c]quinazoline-2,5-dione sodium salt 5.33 ml of 0.1M NaOH were added to a solution of 150 mg (0.533 mmol) of 9-chloro-8-nitro-1-yl-2,3,5,6-tetrahydro[1,2,4]triazolo[4,3-c]quinazoline-3,5-dione and 10 ml of dimethylformamide and the mixture was stirred at room temperature for 30 min. Subsequently, the mixture was filtered, concentrated to dryness, treated 3 times with deionized water and again concentrated. The residue was dried in a high vacuum. There were obtained 142 mg (74%) of 9-chloro-8-nitro-1-yl-2,3,5,6-tetrahydro-[1,2,4]triazolo[1,5-c]quinazoline-2,5-dione sodium salt as a red-brown powder.

MS: me/e=280 (M–Na)⁻.

EXAMPLE 27

9-Fluoro-8-nitro-2,3,5,6-tetrahydro-1,2,4-triazolo[4,3-c]quinazoline-3,5-dione a) 3.8 g (19 mmol) of 2-amino-5-fluoro-4-nitro-benzoic acid were dissolved in 190 ml of ethyl acetate and esterified at 0° C. with diazomethane. The solution was concentrated and the residue was dried. There were obtained: 4.0 g (98%) of methyl 2-amino-5-fluoro-4-nitro-benzoate as yellow crystals;

MS: me/e=214 (M⁺).

b) 4.0 g (18.7 mmol) of methyl 2-amino-5-fluoro-4-nitro-benzoate were dissolved in 250 ml of methanol and saturated with ammonia at –40° C. Subsequently, the mixture was stirred at room temperature overnight. The solution was concentrated and ther residue was triturated with methylene chloride. The precipitate was filtered off under suction and dried. 3.17 g (85%) of 2-amino-5-fluoro-4-nitro-benzamide were obtained as yellow crystals;

MS: me/e=214 (M⁺).

c) 3.1 g (15.6 mmol) of 2-amino-5-fluoro-4-nitro-benzamide were dissolved in 130 ml of tetrahydrofuran and treated at 0° C. with 3.1 g (10.4 mmol) of triphosgene. The mixture was left to warm to room temperature and stirred for a further 1.5 hrs. Then, the solution was concentrated and triturated with water. The precipitate was filtered off under suction and dried. 2.09 g (60%) of 2,4-dioxo-6-fluoro-7-nitro-1,2,3,4-tetrahydroquinazoline were obtained as yellowish crystals;

MS: me/e=225 (M⁺).

d) 2.1 g (9.3 mmol) of 2,4-dioxo-6-fluoro-7-nitro-1,2,3,4-tetrahydroquinazoline were suspended in 12 ml of phosphorus oxychloride and heated to 140° C. for 72 hrs. The reaction mixture was left to cool to room temperature and poured on to ice-water. Subsequently, the mixture was extracted with methylene chloride and the organic phase was dried over magnesium sulphate, filtered and concentrated. The residue was dried and chromatographed over silica gel with methylene chloride as the eluent. 1.69 g (69%) of 2,4-dichloro-6-fluoro-7-nitroquinazoline were obtained as yellow crystals;

MS: me/e=261 (M⁺), 263 (M⁺), 265 (M⁺).

e) 0.98 g (9.2 mmol) of ethyl carbazate was added to a solution of 2.0 g (7.7 mmol) of 2,4-dichloro-6-fluoro-7-nitroquinazoline in 44 ml of dry dimethyl sulphoxide. After 15 min. the mixture was poured on to ice-water. The yellow precipitate was filtered off and dried. 2.13 g (84%) of ethyl 2-chloro-6-fluoro-7-nitro-4-quinazolinecarbazate were obtained as yellow crystals;

MS: me/e=329 (M⁺), 331 (M⁺).

f) A solution of 2.13 g (6.5 mmol) of ethyl 2-chloro-6-fluoro-7-nitro-4-quinazolinecarbazate and 50 ml of dry dimethyl sulphoxide was heated to 100° C. for 1 hr. Subsequently, the mixture was poured on to ice and the yellow precipitate was filtered off and dried. 1.90 g (94%) of ethyl 6-fluoro-7-nitro-2-hydroxy-4-quinazolinecarbazate were obtained as yellow crystals;

MS: me/e=311 (M⁺).

g) 404 mg (1.3 mmol) of ethyl 6-fluoro-7-nitro-2-hydroxy-4-quinazolinecarbazate in 20 ml of dry dimethylformamide were heated at reflux for 2 hrs. The reaction mixture was cooled to room temperature and the solvent was removed on a rotary evaporator. The residue was triturated with a small amount of acetone and the orange coloured precipitate was filtered off and dried in a vacuum. 240 mg (70%) of 9-fluoro-8-nitro-2,3,5,6-tetrahydro-1,2,4-triazolo[4,3-c]quinazoline-3,5-dione were obtained as orange coloured crystals;

MS: me/e=265 (M⁺).

EXAMPLE 28

8-Amino-2,3,5,6-tetrahydro-1,2,4-triazolo[4,3-c]quinazoline-3,5-dione hydrochloride 1.98 g (8.8 mmol) of tin dichloride were dissolved in 10 ml of conc. hydrochloric acid at 80° C. 494 mg (2 mmol) of 8-nitro-2,3,5,6-tetrahydro-1,2,4-triazolo[4,3-c]quinazoline-3,5-dione were added portionwise thereto. After heating at reflux for 2 hrs. the precipitate was filtered off, washed with water and dried in a vacuum. 315 mg (62%) of 8-amino-2,3,5,6-tetrahydro-1,2,4-triazolo[4,3-c]quinazoline-3,5-dione hydrochloride were obtained as white crystals;

MS: me/e=217 (M–HCl)⁺.

EXAMPLE 29

9-Amino-8-chloro-2,3,5,6-tetrahydro-1,2,4-triazolo[4,3-c] quinazoline-3,5-dione

672 mg (2.98 mmol) of tin dichloride were dissolved in 3.4 ml of conc. hydrochloric acid at 80° C. 200 mg (0.71 mmol) of 8-chloro-9-nitro-2,3,5,6-tetrahydro-1,2,4-triazolo [4,3-c]quinazoline-3,5-dione were added portionwise thereto. After heating at reflux for 2 hrs. the precipitate was filtered off, washed with water and dried in a vacuum. 137 mg (67%) of 9-amino-8-chloro-2,3,5,6-tetrahydro-1,2,4-triazolo[4,3-c]quinazoline-3,5-dione hydrochloride were obtained as white crystals;

MS: me/e=251 (M−HCl)$^+$.

EXAMPLE 30

9-Dimethylamino-8-nitro-2,3,5,6-tetrahydro-1,2,4-triazolo [4,3-c]quinazoline-3,5-dione a) A mixture of 500 mg (1.6 mmol) of ethyl 6-fluoro-7-nitro-2-hydroxy-4-quinazoline carbazate and 50 ml of a 33% ethanolic dimethylamine solution was stirred at room temperature for 24 hrs. Subsequently, the solvent was blown off and the residue was taken up in 20 ml of methylene choride. The precipitate was filtered off and dried. 360 mg (67%) of ethyl (6-dimethylamino-7-nitro-2-oxo-1,2-dihydro-quinazolin-4-yl)-carbazate were obtained as an orange coloured powder.

MS: me/e=337 (M+H)$^+$ b) 350 mg (1.04 mmol) of ethyl (6-dimethylamino-7-nitro-2-oxo-1,2-dihydro-quinazolin-4-yl)-carbazate in 30 ml of dry dimethylformamide were heated at reflux for 3 hrs. The reaction mixture was cooled to room temperature and the solvent was removed on a rotary evaporator. The residue was triturated with a small amount of acetone and the red precipitate was filtered off and dried in a vacuum. 195 mg (65%) of 9-dimethylamino-8-nitro-2,3,5,6-tetrahydro-1,2,4-triazolo[4,3-c]quinazoline-3,5-dione were obtained as a red powder.

MS: me/e=291 (M+H)$^+$

EXAMPLE 31

9-Dimethylamino-8-nitro-1-yl-2,3,5,6-tetrahydro-[1,2,4] triazolo[1,5-c]quinazoline-2,5-dione sodium salt

8.05 ml of 0.1M NaOH were added to a solution of 150 mg (0.52 mmol) of 9-dimethylamino-8-nitro-1-yl-2,3,5,6-tetrahydro-[1,2,4]triazolo[4,3-c]quinazoline-3,5-dione and 20 ml of dimethylformamide and the mixture was stirred at room temperature for 30 min. Subsequently, the mixture was concentrated to dryness, treated 3 times with deionized water and again concentrated. The residue was dried in a high vacuum. There were obtained 123 mg (76%) of 9-dimethylamino-8-nitro-1-yl-2,3,5,6-tetrahydro-[1,2,4] triazolo[1,5-c]quinazoline-2,5-dione sodium salt as a red-brown powder.

MS: me/e=289 (M−Na)$^-$.

EXAMPLE 32

8-Nitro-9-pyrrolidin-1-yl-2,3,5,6-tetrahydro-1,2,4-triazolo [4,3-c]quinazoline-3,5-dione a) A mixture of 500 mg (1.6 mmol) of ethyl 6-fluoro-7-nitro-2-hydroxy-4-quinazolinecarbazate and 50 ml of pyrrolidine was stirred at room temperature for 4 hrs. Subsequently, the solvent was blown off and the residue was chromatographed over silica gel with methylene chloride/methanol 95:5 as the eluent. 512 mg (88%) of ethyl (7-nitro-2-oxo-6-pyrrolidin-1-yl-1,2-dihydro-quinazolin-4-yl)-carbazate were obtained as a red powder.

MS: me/e=363 (M+H)$^+$ b) 500 mg (1.38 mmol) of ethyl (7-nitro-2-oxo-6-pyrrolidin-1-yl-1,2-dihydro-quinazolin-4-yl)-carbazate in 30 ml of dry dimethylformamide were heated at reflux for 3 hrs. The reaction mixture was cooled to room temperature and the solvent was removed on a rotary evaporator. The residue was triturated with a small amount of acetone and the red precipitate was filtered off and dried in a vacuum. 342 mg (78%) of 8-nitro-9-pyrrolidin-1-yl-2,3,5,6-tetrahydro-1,2,4-triazolo[4,3-c]quinazoline-3,5-dione were obtained as a red powder.

MS: me/e=317 (M+H)$^+$.

EXAMPLE 33

8-Nitro-9-pyrrolidin-1-yl-2,3,5,6-tetrahydro-[1,2,4]triazolo [1,5-c]quinazoline-2,5-dione sodium salt,

9.86 ml of 0.1M NaOH were added to a solution of 200 mg (0.63 mmol) of 8-nitro-9-pyrrolidin-1-yl-2,3,5,6-tetrahydro[1,2,4]triazolo[4,3-c]quinazoline-3,5-dione and 20 ml of dimethylformamide and the mixture was stirred at room temperature for 30 min. Subsequently, the mixture was concentrated to dryness, treated 3 times with deionized water and again concentrated. The residue was dried in a high vacuum. There were obtained 193 mg (90%) of 8-nitro-9-pyrrolidin-1-yl-2,3,5,6-tetrahydro-[1,2,4]triazolo[1,5-c] quinazoline-2,5-dione as a red-brown powder.

MS: me/e=315 (M−Na)$^-$.

EXAMPLE 34

9-Morpholin-4-yl-8-nitro-2,3,5,6-tetrahydro-1,2,4-triazolo [4,3-c]quinazoline-3,5-dione a) A mixture of 500 mg (1.6 mmol) of ethyl 6-fluoro-7-nitro-2-hydroxy-4-quinazolinecarbazate and 10 ml of morpholine was stirred at room temperature for 4 hrs. Subsequently, the solvent was blown off and the residue was taken up in 20 ml of methylene chloride. The precipitate was filtered off and dried. 360 mg (59%) of ethyl (6-morpholin-4-yl-7-nitro-2-oxo-1,2-dihydroquinazolin-4-yl)-carbazate were obtained as an orange coloured powder.

MS: me/e=378 (M$^+$).

b) 145 mg (0.38 mmol) of ethyl (6-morpholin-4-yl-7-nitro-2-oxo-1,2-dihydro-quinazolin-4-yl)-carbazate in 20 ml of dry dimethylformamide were heated at reflux for 2 hrs. The reaction mixture was cooled to room temperature and the solvent was removed on a rotary evaporator. The residue was triturated with a small amount of acetone and the red precipitate was filtered off and dried in a vacuum. 76 mg (60%) of 9-morpholin-4-yl-8-nitro-2,3,5,6-tetrahydro-1,2,4-triazolo[4,3-c]quinazoline-3,5-dione were obtained as a brown-red powder.

MS: me/e=333 (M+H)$^+$.

EXAMPLE 35

9-(4-Methyl-piperazin-1-yl)-8-nitro-2,3,5,6-tetrahydro-1, 2,4-triazolo[quinazoline-3,5-dione a) A mixture of 150 mg (0.48 mmol) of ethyl 6-fluoro-7-nitro-2-hydroxy-4-quinazolinecarbazate and 5 ml of N-methylpiperazine was stirred at room temperature for 3 hrs. Subsequently, the solvent was blown off and the residue was taken up in 20 ml of methylene chloride. The precipitate was filtered off and dried. 90 mg (48%) of ethyl 3-[6-(4-methyl-piperazin-1-yl)-7-nitro-2-oxo-1,2-dihydroquinazolin-4-yl]-carbazate were obtained as an orange coloured powder.

MS: me/e=392 (M+1)⁺.

b) 73 mg (0.19 mmol) of ethyl 3-[6-(4-methyl-piperazin-1-yl)-7-nitro-2-oxo-1,2-dihydro-quinazolin-4-yl]-carbazate in 3 ml of dry dimethyl sulphoxide were heated to 150° C. for 2 hrs. Subsequently, the solvent was blown off and the residue was triturated with a small amount of acetone. The precipitate was filtered off and dried in a vacuum. 49 mg (73%) of 9-(4-methylpeperazin-1-yl)-8-nitro-2,3,5,6-tetrahydro-1,2,4-triazolo-[4,3-c]quinazoline-3,5-dione were obtained as an orange-brown powder.

MS: me/e=346 (M+H)⁺.

EXAMPLE 36 a) 9-Imidazol-1-yl-8-nitro-2,3,5,6-tetrahydro-[1,2,4]-triazolo[1,5-c]quinazoline-2,5-dione salt with imidazole (1:1)

A mixture of 500 mg (1.6 mmol) of ethyl 6-fluoro-7-nitro-2-hydroxy-4-quinazolinecarbazate and 7.5 g (110 mmol) of imidazole was heated to 100° C. for 3 hrs. Subsequently, 80 ml of methanol were added and the yellow precipitate was filtered off and dried. 547 mg (89%) of 9-imidazol-1-yl-8-nitro-2,3,5,6-tetrahydro-[1,2,4]triazolo[1,5-c]quinazoline-2,5-dione salt with imidazole were obtained.

MS: me/e=314 (M+H)⁺.

b) 9-Imidazol-1-yl-8-nitro-2,3,5,6-tetrahydro-[1,2,4]triazolo[1,5-c]quinazoline-2,5-dione sodium salt (1:1)

5.3 ml of 0.1M NaOH were added to a solution of 200 mg (0.52 mmol) of 9-imidazol-1-yl-8-nitro-2,3,5,6-tetrahydro [1,2,4]triazolo[1,5-c]quinazoline-2,5-dione salt with imidazole (1:1) and 40 ml of dimethylformamide and the mixture was stirred at room temperature for 30 min. Subsequently, the mixture was concentrated to dryness and treated 3 times with deionized water and concentrated. The residue was dried in a high vacuum. There were obtained 134 mg (76%) of 9-imidazol-1-yl-8-nitro-2,3,5,6-tetrahydro-[1,2,4]triazolo [1,5-c]quinazoline-2,5-dione sodium salt as an orange powder.

MS: me/e=314 (M−Na+H)⁺.

c) 9-Imidazol-1-yl-8-nitro-2,3,5,6-tetrahydro-[1,2,4]-triazolo[1,5-c]quinazoline-2,5-dione 2M HCl was added dropwise to a solution of 300 mg (0.84 mmol) of 9-imidazol-1-yl-8-nitro-2,3,5,6-tetrahydro[1,2,4]triazolo[1,5-c]quinazoline-2,5-dione and 20 ml of water until the solution had a pH of 1. The precipitate was filtered off under suction and dried. There were obtained 242 mg (91%) of 9-imidazol-1-yl-8-nitro-2,3,5,6-tetrahydro-[1,2,4]triazolo[1,5-c]quinazoline-2,5-dione as an orange powder.

MS: me/e=314 (M+H)⁺.

d) 9-Imidazol-1-yl-8-nitro-2,3,5,6-tetrahydro-[1,2,4]triazolo [4,3-c]quinazoline-3,5-dione A solution of 100 mg (0.32 mmol) of 9-imidazol-1-yl-8-nitro-2,3,5,6-tetrahydro-[1,2,4]triazolo[1,5-c]quinazoline-2, 5-dione and 10 ml of DMF was heated to 80° C. for 30 min. and subsequently concentrated to dryness. After trituration with acetone the residue was filtered off under suction. There were obtained 84 mg (84%) of 9-imidazol-1-yl-8-nitro-2,3, 5,6-tetrahydro-[1,2,4]triazolo[4,3-c]quinazoline-3,5-dione.

MS: me/e=314 (M+H)⁺.

EXAMPLE 37

8,9-Dinitro-2,3,5,6-tetrahydro-1,2,4-triazolo[4,3-c] quinazoline-3,5-dione a) 10 g (48.3 mmol) of 7-nitro-1,2,3,4-tetrahydro-quinazoline-2,4-dione were added portionwise at 0° C. to 32 ml of fuming nitric acid. Thereafter, the mixture was stirred at room temperature for a further 5 hrs. The reaction mixture was poured on to ice, the precipitate was filtered off under suction and washed with 65% nitric acid, dilute nitric acid and finally with water. 7.15 g (59%) of 6,7-dinitro-1,2,3,4-tetrahydroquinazoline-2,4-dione were obtained as a yellow powder;

MS: me/e=252 (M⁺).

b) 2 g (7.9 mmol) of 6,7-dinitro-1,2,3,4-tetrahydro-quinazoline-2,4-dione were suspended in 12 ml of phosphorus oxychloride and heated to 140° C. for 96 hrs. After cooling to room temperature the reaction mixture was concentrated to dryness. The residue was chromatographed over silica gel with methylene chloride as the eluent. 1.11 g (48%) of 2,4-dichloro-6,7-dinitroquinazoline were obtained as yellow crystals;

MS: me/e=288 (M⁺), 290 (M⁺), 292 (M⁺).

c) 0.475 g (4.57 mmol) of ethyl carbazate was added to a solution of 1.1 g (3.8 mmol) of 2,4-dichloro-6,7-dinitroquinazoline in 25 ml of dry dimethyl sulphoxide. After 15 min. the mixture was poured on to ice-water. The orange coloured precipitate was filtered off and dried. 1.12 g (83%) of ethyl 2-chloro-6,7-dinitro-4-quinazolinecarbazate were obtained as orange coloured crystals;

MS: me/e=356 (M⁺).

d) A solution of 1.1 g (3.1 mmol) of ethyl 2-chloro-6,7-dinitro-4-quinazolinecarbazate and 25 ml of dry dimethyl sulphoxide was heated to 100° C. for 1 hr. Subsequently, the mixture was poured on to ice and the yellow precipitate was filtered off and dried. 0.82 g (79%) of ethyl 6,7-dinitro-2-hydroxy- 4-quinazolinecarbazate was obtained as yellow crystals;

MS: me/e=338 (M⁺).

e) 810 mg (2.39 mmol) of ethyl 6,7-dinitro-2-hydroxy-4-quinazolinecarbazate in 30 ml of dry dimethylformamide were heated at reflux for 3 hrs. The reaction mixture was cooled to room temperature and the solvent was removed on a rotary evaporator. The residue was triturated with a small amount of acetone, the orange coloured precipitate was filtered off and dried in a vacuum. 560 mg (80%) of 8,9-dinitro-2,3,5,6-tetrahydro-1,2,4-triazolo[4,3-c] quinazoline-3,5-dione were obtained as orange crystals;

MS: me/e=292 (M⁺).

EXAMPLE 38

9-Bromo-8-nitro-2,3,5,6-tetrahydro-1,2,4-triazolo[4,3-c] quinazoline-3,5-dione a) 25.8 g (93.8 mmol) of methyl 2-amino-5-bromo-4-nitro-benzoate were dissolved in 800 ml of methanol and saturated with ammonia at −40° C. Subsequently, the mixture was stirred at room temperature overnight. The solution was concentrated and the residue was triturated with methylene chloride. The precipitate was filtered off under suction and dried. 18.3 g (75%) of 2-amino-5-bromo-4-nitro-benzamide were obtained as orange coloured crystals;

MS: me/e=259 (M⁺), 261 (M⁺).

b) 17.3 g (66.5 mmol) of 2-amino-5-bromo-4-nitro-benzamide were dissolved in 500 ml of tetrahydrofuran and treated at 0° C. with 13 g (10.4 mmol) of triphosgene. The mixture was left to warm to room temperature and stirred for a further 1.5 hrs. Then, the solution was concentrated and triturated with water. The precipitate was filtered off under suction and dried. 8.6 g (45%) of 2,4-dioxo-6-bromo-7-nitro-1,2,3,4-tetrahydroquinazoline were obtained as yellowish crystals;

MS: m/e=285 (M$^+$), 287 (M$^+$)

c) 8.6 g (30.1 mmol) of 2,4-dioxo-6-bromo-7-nitro-1,2,3,4-tetrahydroquinazoline were suspended in 42 ml of phosphorus oxychloride and heated to 140° C. for 96 hrs. After cooling to room temperature the reaction mixture was concentrated to dryness. The residue was chromatographed over Florisil with methylene chloride as the eluent. 2.8 g (29%) of 2,4-dichloro-6-bromo-7-nitroquinazoline were obtained as pale yellow crystals;

MS: m/e=321 (M$^+$), 323 (M$^+$), 325 (M$^+$), 327 (M$^+$).

d) 1.0 g (9.6 mmol) of ethyl carbazate was added to a solution of 2.6 g (8.1 mmol) of 2,4-dichloro-6-bromo-7-nitroquinazoline in 45 ml of dry dimethyl sulphoxide. After 15 min. the mixture was poured on to ice-water. The yellow precipitate was filtered off and dried. 2.88 g (91%) of ethyl 2-chloro-6-bromo-7-nitro-4-quinazolinecarbazate were obtained as yellow crystals;

MS: m/e=389 (M$^+$), 391 (M$^+$), 393 (M$^+$).

e) A solution of 2.88 g (7.37 mmol) of ethyl 6-bromo-7-nitro-2-hydroxy-4-quinazolinecarbazate and 55 ml of dry dimethyl sulphoxide was heated to 100° C. for 1 hr. Subsequently, the mixture was poured on to ice and the yellow precipitate was filtered off and dried. 2.47 g (90%) of ethyl 6-bromo-7-nitro-2-hydroxy-4-quinazolinecarbazate were obtained as yellow crystals;

MS: m/e=372 (M+H)$^+$, 374 (M+H)$^+$.

f) 2.45 g (6.6 mmol) of ethyl 6-bromo-7-nitro-2-hydroxy-4-quinazolinecarbazate in 150 ml in 150 ml of dry dimethylformamide were heated at reflux for 2 hrs. The reaction mixture was cooled to room temperature and the solvent was removed on a rotary evaporator. The residue was triturated with a small amount of acetone, the orange coloured precipitate was filtered off and dried in a vacuum. 1.3 g (61%) of 9-bromo-8-nitro-2,3,5,6-tetrahydro-1,2,4-triazolo[4,3-c]quinazoline-3,5-dione were obtained as an orange coloured powder;

MS: m/e=325 (M$^+$), 327 (M$^+$).

Preparation of the compounds of formula II

EXAMPLE 39

5-Hydroxy-3,4-dihydro-pyrido[3,4-c]quinolin-4-one a) A mixture of 4.34 g (0.022 mol) of 2-methoxy-4-methylquinoline-3-carbonitrile and 7.8 g (0.066 mol) of N,N-dimethylformamide dimethyl acetal was boiled under slight reflux under argon for 65 hrs. The mixture was cooled and chromatographed over silica gel with dichloromethane as the eluent. The product was recrystallized from methanol. Renewed chromatography of the mother liquor and subsequent recrystallization gave additional product. Yield: 4.22 g (76%) of (E)-4-(2-dimethyl-amino-vinyl)-2-methoxy-quinoline-3-carbonitrile as yellow crystals; m.p. 101°–103° C.

b) 3.33 g (0.013 mol) of (E)-4-(2-dimethyl-amino-vinyl)-2-methoxy-quinoline-3-carbonitrile were boiled under reflux for 2 hrs. in a solvent mixture of 4.6 ml of sulphuric acid, 29 ml of acetic acid and 9.6 ml of water. The reaction mixture was cooled to room temperature and then poured on to 115 ml of ice-water. The precipitate was filtered off, washed with water, dried in a vacuum and recrystallized from dimethylformamide/methanol. Yield: 1.83 g (65%) of 5-hydroxy-3,4-dihydro-pyrido[3,4-c]quinolin-4-one as light yellow crystals; m.p. 312°–327° C. (subl.).

EXAMPLE 40

8-Chloro-5-hydroxy-3,4-dihydro-pyrido[3,4-c]quinoline-4-one a) A mixture of 6.5 g (0.038 mol) of 1-(2-amino-4-chlorophenyl)-ethanone and 5.2 g (0.046 mol) of ethyl cyanoacetate was heated to 200° C. for 4 hrs., with a water/ethanol mixture formed being distilled off. The mixture was stirred at 210° C. for a further 2 hrs., left to cool to room temperature, the resulting brown mass was ground in a mortar, suspended in ethanol overnight, filtered off, washed with ethanol and dried in a vacuum. Yield: 7.28g (87%) of 7-chloro-2-hydroxy-4-methyl-quinoline-3-carbonitrile as pale brown crystals; m.p. >350° C.

MS: m/e (% base peak)=218 ($C_{11}H_7ClN_2O^+$, 100), 190 (53), 189 (35), 163 (7.5), 155(13), 140(4), 128(11), 101 (6), 77 (20).

b) 7.58 g (0.035 mol) of 7-chloro-2-hydroxy-4-methyl-quinoline-3-carbonitrile were suspended in 32 ml (0.347 mol) of phosphorus oxichloride and stirred at 105° C. for 4 hrs. The excess phosphorus oxichloride was distilled off. The residue was partitioned between 1 l of ethyl acetate and 0.5 l of water and filtered off over Dicalite. Extraction with ethyl acetate, drying over magnesium sulphate, filtration and concentration then followed. The product was recrystallized from hot methanol. Yield: 7.4 g (90%) of 2,7-dichloro-4-methyl-quinoline-3-carbonitrile as white crystals; m.p. 153°–154° C.

c) 7.4 g (0.035 mol) of 2,7-dichloro-4-methyl-quinoline-3-carbonitrile were suspended in 600 ml of methanol. 6.3 g (0.275 mol) of sodium were added portionwise thereto at 40° C. and the mixture was boiled under reflux for 16 hrs. The mixture was cooled to 40° C., 300 ml of water were slowly added thereto and the mixture was stirred in an ice bath for ½ hr. The suspension obtained was filtered off, washed with water and dried in a vacuum. Yield: 6.0 g (83%) of 7-chloro-2-methoxy-4-methyl-quinoline-3-carbonitrile as white crystals; m.p. 183°–185° C.

d) A mixture of 6.0 g (0.026 mol) of 7-chloro-2-methoxy-4-methyl-quinoline-3-carbonitrile and 30.7 g (0.258 mol) of N,N-dimethylformamide dimethyl acetal was boiled under slight reflux for 23 hrs. (after 19 hrs. a further 15.4 g (0.129 mol) of N,N-dimethylformamide dimethyl acetal were added thereto). The mixture was cooled and chromatographed over silica gel with dichloromethane/n-hexane 4:1 as the eluent. The product was recrystallized from ethyl acetate. One recrystallization of the mother liquor gave additional product. Yield: 4.0 g (54%) of (E)-7-chloro-4-(2-dimethyl-amino-vinyl)-2-methoxy-quinoline-3-carbonitrile as yellow crystals; m.p. 174°–175° C.

e) 2.5 g (0.0087 mol) of (E)-7-chloro-4-(2-dimethyl-amino-vinyl)-2-methoxy-quinoline-3-carbonitrile were boiled under reflux for 2 hrs. in a solvent mixture of 3 ml of sulphuric acid, 19 ml of acetic acid and 6.3 ml of water. The reaction mixture was cooled to 0° C. and then poured on to 80 ml of ice-water. The precipitate was filtered off, washed with water, dried in a vacuum and recrystallized from dimethylformamide/ethyl acetate. Yield: 1.26 g (59%) of 8-chloro-5-hydroxy-3,4-dihydropyrido[3,4-c]quinolin-4-one as beige crystals; m.p. 340°–342° C.

EXAMPLE 41

8,9-Dichloro-5-hydroxy-3,4-dihydro-pyrido[3,4-c]quinolin-4-one a) A mixture of 29.6 g (0.145 mol) of 1-(2-amino-4,5-dichloro-phenyl)-ethanone and 19.7 g (0.174 mol) of ethyl-cyanoacetate was heated to 210° C. for 6 hrs., with a water/ethanol mixture formed being distilled off. The mixture was left to cool to room temperature, the resulting brown mass was ground in a mortar, suspended in ethanol overnight, filtered off, washed with ethanol and dried in a vacuum. Yield: 30.2 g (82%) of 6,7-dichloro-2-hydroxy-4-methyl-quinoline-3-carbonitrile as pale brown crystals. An analytical sample could be recrystallized from the ethanolic phase; m.p. 310°–315° C. (dec.).

b) 15 g (0.059 mol) of 6,7-dichloro-2-hydroxy-4-methyl-quinoline-3-carbonitrile were suspended in 54 ml (0.59 mol) of phosphorus oxychloride and stirred at 105° C. for 3 hrs. The excess phosphorus oxychloride was distilled off. The residue was partitioned between 1 l of ethyl acetate and 0.5 l of water and filtered over Dicalite. Extraction with ethyl acetate, drying over magnesium sulphate, filtration and concentration followed. The product was recrystallized from hot methanol. Yield: 10.7 g (66%) of 2,6,7-trichloro-4-methyl-quinoline-3-carbonitrile as white crystals; m.p. 195°–197° C.

c) 10.7 g (0.039 mol) of 2,6,7-trichloro-4-methyl-quinoline-3-carbonitrile were suspended in 1 l of methanol. 8.0 g (0.35 mol) of sodium were added portionwise thereto at 40° C. and the mixture was boiled under reflux for 16 hrs. The mixture was cooled to 40° C. and 0.5 l of water was slowly added thereto. The suspension obtained was filtered, washed with water and dried in a vacuum. The crude product was recrystallized from ethyl acetate. Yield: 7.42 g (71%) of 6,7-dichloro-2-methoxy-4-methyl-quinoline-3-carbonitrile as white crystals; m.p. 179°–181° C.

d) A mixture of 7.42 g (0.028 mol) of 6,7-dichloro-2-methoxy-4-methyl-quinoline-3-carbonitrile and 33.1 g (0.278 mol) of N,N-dimethylformamide dimethyl acetal was boiled under slight reflux for 17 hrs. The mixture was concentrated totally and the residue was recrystallized from hot ethyl acetate. Recrystallization of the mother liquor gave additional product. Yield: 6.63 g (74%) of (E)-6,7-dichloro-4-(2-dimethyl-amino-vinyl)-2-methoxy-quinoline-3-carbonitrile as pale greenish crystals; m.p. 230°–232° C.

e) 2.2 g (0.0069 mol) of (E)-6,7-dichloro-4-(2-dimethyl-amino-vinyl)-2-methoxy-quinoline-3-carbonitrile were boiled under reflux for 2 hrs. in a solvent mixture of 2.4 ml of sulphuric acid, 15 ml of acetic acid and 5.0 ml of water. The reaction mixture was cooled to room temperature and then poured on to 150 ml of ice-water. The precipitate was filtered off, washed with water, dried in a vacuum and recrystallized from dimethylformamide. Yield: 1.36 g (70%) of 8,9-dichloro-5-hydroxy-3,4-dihydro-pyrido[3,4-c] quinolin-4-one as pale yellow crystals; m.p. >350° C.

MS: me/e (% base peak)=280 ($C_{12}H_6Cl_2N_2O_2^+$, 90), 252 (100), 223 (14), 189 (31), 162 (18), 127 (15), 111 (16), 97 (22), 81 (29), 69 (43), 55 (44), 41 (52).

EXAMPLE 42

5-Hydroxy-3,4-dihydro-pyridazino[4,5-c]quinolin-4-one a) 6.1 g (0.021 mol) of ethyl 4-dimethoxymethyl-2-hydroxy-quinoline-3-carboxylate (E. Ziegler, T. Kappe, H. G. Foraita, *Monatsh. Chem.* 1966, 97, 409) were suspended in 60 ml of 6N aqueous hydrochloric acid and boiled under reflux for 3 minutes. The mixture was cooled to 0° C., treated with 150 ml of water, suction filtered and rinsed with water, methanol and ethyl acetate. Yield: 3.5 g (77%) of (RS)-1,4-dihydroxy-1,3-dihydrofuro[3,4-c]quinolin-3-one as light greenish crystals; m.p. 295°–302° C. (dec.).

b) 0.54 g (0.0025 mol) of (RS)-1,4-dihydroxy-1,3-dihydrofuro[3,4-c]quinolin-3-one was dissolved in 5 ml of dimethyl sulphoxide while gassing with argon. 0.125 g (0.0025 mol) of hydrazine hydrate was added thereto and the mixture was stirred at room temperature for 4 days. The suspension obtained was suction filtered and rinsed with ethyl acetate. Yield: 0.28 g (53%) of 5-hydroxy-3,4-dihydro-pyridazino[4,5-c]quinolin-4-one as yellow crystals; m.p. >350° C.

MS: me/e (% base peak)=213 ($C_{11}H_7N_3O_2^+$, 100), 185 (46), 157 (18), 129 (32), 102 (17), 75 (10).

EXAMPLE 43

8-Chloro-5-hydroxy-3,4-dihydro-pyridazino [4,5-c] quinolin-4-one a) 16. g (0.083 mol) of a mixture of 7-chloro-quinoline-2,4-diol/5-chloro-quinoline-2,4-diol~1:2 (T. Kappe, A. S. Karem, W. Stadlbauer, *J. Heterocycl. Chem.* 1988, 28, 857) were suspended in 80 ml of dioxan. 9.4 g (0.17 mol) of sulphuryl chloride were added dropwise thereto at 50° C. within 10 minutes and the mixture was boiled under reflux for 20 minutes. The mixture was cooled, poured on to 300 ml of ice-water, extracted with ethyl acetate and chromatographed over silica gel with toluene/ethyl acetate 19:1 as the eluent. Both products were recrystallized from ether/n-hexane. Yield: 8.8 g (40%) of 3,3,7-trichloro-1,2,3,4-tetrahydro-quinoline-2,4-dione as yellow-orange crystals; m.p. 235°–236° C., and 10.7 g (49%) of 3,3,5-trichloro-1,2,3,4-tetrahydro-quinoline-2,4-dione as yellow crystals; m.p. 194°–196° C.

b) 3.5 g (0.15 mol) of sodium were dissolved in 75 ml of methanol while gassing with argon. A warm solution of 13.4 g (0.051 mol) of 3,3,7-trichloro-1,2,3,4-tetrahydro-quinoline-2,4-dione in 140 ml of methanol was added dropwise thereto at 65° C. within 20 minutes. The mixture was boiled under reflux for 15 minutes, treated with 150 ml of 2N aqueous sodium hydroxide solution and distilled until an internal temperature of 100° C. had been attained. The mixture was cooled, extracted with ethyl acetate, recrystallized from ether/n-hexane and the mother liquor was chromatographed over silica gel with n-hexane/ethyl acetate 1:2 as the eluent. Yield: 8.9 g (77%) of 1-(2-amino-4-chloro-phenyl)-2,2-dimethoxy-ethanone as yellowish crystals; m.p. 81°–82° C.

c) 8.9 g (0.039 mol) of 1-(2-amino-4-chloro-phenyl)-2,2-dimethoxy-ethanone were suspended in 31 g (0.19 mol) of diethyl malonate and stirred at 170° C. for 18 hrs. The mixture was cooled, diluted with 50 ml of ethyl acetate/n-hexane 1:1, filtered, concentrated and chromatographed over silica gel with n-hexane/ethyl acetate 1:1 as the eluent. The product was recrystallized from ethyl acetate/n-hexane. Yield: 6.63 g (53%) of ethyl 7-chloro-4-dimethoxymethyl-2-hydroxy-quinoline-3-carboxylate as white crystals; m.p. 134°–136° C.

d) 6.63 g (0.020 mol) of ethyl 7-chloro-4-dimethoxymethyl-2-hydroxy-quinoline-3-carboxylate were suspended in 70 ml of 25% aqueous hydrochloric acid and boiled under reflux for 30 minutes. The mixture was cooled to 0° C., treated with 200 ml of water, suction filtered, rinsed with water and ethyl acetate and dried in a vacuum. The product was recrystallized from dimethylformamide/ethyl acetate. Yield: 3.85 g (75%) of (RS)-7-chloro- 1,4- dihydroxy-1,3-dihydro-furo[3,4-c]quinolin-3-one as light beige crystals; m.p. 270°–310° C. (dec.).

MS: me/e (% base peak)=251 ($C_{11}H_6ClNO_4^+$, 31), 223 (45), 205 (100), 179 (80), 177 (64), 151 (43), 149 (43), 114 (44).

e) 2.0 g (0.0079 mol) of (RS)-7-chloro-1,4-dihydroxy-1,3-dihydro-furo[3,4-c]quinolin-3-one were dissolved in 20 ml of dimethyl sulphoxide while gassing with argon. 0.40 g (0.0062 mol) of hydrazine hydrate was added thereto and the mixture was stirred at room temperature for 90 hrs. The suspension obtained was suction filtered and rinsed with ethyl acetate. Yield: 1.21 g (61%) of 8-chloro-5-hydroxy-3,4-dihydropyridazino[4,5-c]quinolin-4-one as yellow crystals; m.p. >350° C.

MS: me/e (% base peak)=247 ($C_{11}H_6N_3O_2^+$, 100), 219 (57), 191 (15), 163 (23), 128 (22), 99 (13).

EXAMPLE 44

8,9-Dichloro-5-hydroxy-3,4-dihydro-pyridazino[4,5-c]quinolin-4-one a) 169.8 g (0.738 mol) of a mixture of 6,7-dichloro-quinoline-2,4-diol/5,6-dichloro-quinoline-2,4-diol~1:9 (T. Kappe, A. S. Karem, W. Stadlbauer, *J. Heterocycl. Chem.* 1988, 28, 857) were suspended in 700 ml of dioxan. 274 g (2.03 mol) of sulphuryl chloride were added dropwise thereto at 50° C. within ¾ hr. and the mixture was stirred at 90° C. for 15 min. The mixture was cooled, poured on to 4 l of ice-water and extracted with ethyl acetate. Yield: 204 g (93%) of a crude mixture, 3,3,6,7-tetrachloro-1,2,3,4-tetrahydro-quinoline-2,4-dione/3,3,5,6-tetrachloro-1,2,3,4-tetrahydro-quinoline-2,4-dione~1:9, as yellow crystals.

b) 47.1 g (2.05 mol) of sodium were dissolved in 1 l of methanol while gassing with argon. A warm solution of 204 g (0.68 mol) of a crude mixture of 3,3,6,7-tetrachloro-1,2,3,4-tetrahydro-quinoline- 2,4-dione/3,3,5,6 -tetrachloro-1,2,3,4-tetrahydro-quinoline-2,4-dione ~1:9 in 1.2 l of methanol was added dropwise thereto at 65° C. within 20 minutes. The mixture was boiled under reflux for 10 minutes, treated with 2 l of 2N aqueous sodium hydroxide solution and distilled until an internal temperature of 100° C. had been attained. The mixture was cooled, extracted with ethyl acetate and chromatographed over silica gel with n-hexane/ethyl acetate 4:1 as the eluent. Both products were recrystallized from ether/n-hexane. Yield: 22.7 g (13%) of 1-(2-amino-4,5-dichloro-phenyl)-2,2-dimethoxy-ethanone as yellowish crystals; m.p. 91°–92° C., and 45.3 g (25%) of 1-(2-amino-5,6-dichloro-phenyl)-2,2-dimethoxy-ethanone as yellow crystals; m.p. 81°–82° C.

c) 22.7 g (0.086 mol) of 1-(2-amino-4,5-dichloro-phenyl)-2,2-dimethoxy-ethanone were suspended in 69 g (0.43 mol) of diethyl malonate and stirred at 170° C. for 15 hrs. The mixture was cooled, diluted with 50 ml of ethyl acetate and chromatographed several times over silica gel with n-hexane/ethyl acetate 3:1 as the eluent. The product was dissolved in hot ethyl acetate and recrystallized by the addition of n-hexane. 7.6 g (33%) of educt were obtained as an orange coloured oil. Yield: 3.1 g (15%) of ethyl 6,7-dichloro-4-dimethoxymethyl-2-hydroxy-quinoline-3-carboxylate as whitish crystals; m.p. 198°–200° C.

d) 4.7 g (0.013 mol) of ethyl 6,7-dichloro-4-dimethoxymethyl-2-hydroxy-quinoline-3-carboxylate were suspended in 50 ml of 2.5 percent aqueous hydrochloric acid and stirred at 100° C. for 30 minutes. The mixture was cooled to 0° C., treated with 150 ml of water, suction filtered and dried in a vacuum. The product was recrystallized from dimethylformamide/ethyl acetate. Yield: 2.90 g (78%) of (RS)-7,8-dichloro-1,4-dihydroxy-1,3-dihydrofuro[3,4-c]quinolin-3-one as beige-brownish crystals; m.p. ~275° C. (dec.).

e) 1.76 g (0.0062 mol) of (RS)-7,8-dichloro-1,4-dihydroxy-1,3-dihydro-furo[3,4-c]quinolin-3-one were dissolved in 18 ml of dimethyl sulphoxide while gassing with argon. 0.31 g (0.0062 mol) of hydrazine hydrate was added thereto and the mixture was stirred at room temperature for 42 hrs. The suspension obtained was suction filtered and rinsed with ethyl acetate. Yield: 0.32 g (18%) of 8,9-dichloro-5-hydroxy-3,4-dihydro-pyridazino[4,5-c]quinolin-4-one as yellow crystals; m.p. >350° C.

MS: me/e (% base peak)=281 ($C_{11}H_5Cl_2N_3O_2^+$, 100), 253 (62), 225 (16), 197 (37), 162 (29), 124 (13), 99 (19).

EXAMPLE 45

9,10-Dichloro-5-hydroxy-3,4-dihydro-pyridazino[4,5-c]quinolin-4-one a) 13.1 g (0.050 mol) of 1-(2-amino-5,6-dichloro-phenyl)-2,2-dimethoxy-ethanone were dissolved in 250 ml of dichloromethane and treated with 5.5 g (0.055 mol) of triethylamine. 8.2 g (0.055 mol) of ethylmalonyl chloride were added dropwise at 0° C. within 15 minutes. The mixture was stirred at 0° C. for a further 15 minutes, treated with 150 ml of water, extracted with dichloromethane and chromatographed over silica gel firstly with dichloromethane/n-hexane 4:1, then with methanol as the eluent. The methanolic fractions were concentrated, taken up in hot ethyl acetate, filtered and concentrated. The residue was recrystallized from ether/n-hexane. Yield: 10.2 g (54%) of racemic ethyl (cis and/or trans)-5,6-dichloro-4-dimethoxymethyl-2,4-dihydroxy-3,4-dihydro-quinoline-3-carboxylate as white crystals; m.p. 265°–270° C. (dec.).

b) 5.0 g (0.013 mol) of racemic ethyl (cis and/or trans)-5,6-dichloro-4-dimethoxymethyl-2,4-dihydroxy-3,4-dihydro-quinoline-3-carboxylate were suspended in a mixture of 84 ml of acetic acid, 28 ml of water and 14 ml of sulphuric acid and stirred at 100° C. for 16 hrs. The mixture was cooled, treated with 400 ml of water, suction filtered and dried in a vacuum. The product was dissolved in hot dimethylformamide, filtered, partially concentrated and recrystallized by the addition of ethyl acetate. Yield: 2.95 g (78%) of (RS)-8,9-dichloro-1,4-dihydroxy-1,3-dihydro-furo [3,4-c]quinolin-3-one as yellowish crystals; m.p. 285°–290° C. (dec.).

c) 2.9 g (0.010 mol) of (RS)-8,9-dichloro-1,4-dihydroxy-1,3-dihydro-furo[3,4-c]quinolin-3-one were dissolved in 60 ml of dimethyl sulphoxide while gassing with argon. 0.51 g (0.010 mol) of hydrazine hydrate was added thereto and the mixture was stirred at room temperature for 50 hrs. An orange coloured solution was obtained and this was treated with 300 ml of ethyl acetate. The precipitated product was filtered off under suction, rinsed with ethyl acetate and recrystallized from dimethylformamide/ethyl acetate. Yield: 0.70 g (25%) of 9,10-dichloro-5-hydroxy-3,4-dihydro-pyridazino[4,5-c]quinolin-4-one as yellow-orange coloured crystals; m.p. ~270° C.

MS: me/e (% base peak)=281 ($C_{11}H_5Cl_2N_3O_2^+$, 100), 253 (60), 239 (19), 213 (40), 185 (15), 162 (2:3), 148 (16), 123 (16), 45 (58).

EXAMPLE 46

8,10-Dichloro-5-hydroxy-3,4-dihydro-pyridazino[4,5-c]quinolin-4-one a) 9.1 g (0.040 mol) of 5,7-dichloro-quinoline-2,4-diol (prepared as similar substances in: T. Kappe, A. S. Karem, W. Stadlbauer, *J. Heterocycl. Chem.* 1988, 28, 857) were suspended in 60 ml of dioxan. 14.7 g (0.11 mol) of sulphuryl chloride were added dropwise thereto at 50° C. within 10 minutes and the mixture was boiled under reflux for 10 minutes. The mixture was cooled, poured on to 150 ml of ice-water and extracted with ethyl acetate. An analytical sample was recrystallized from methanol. Yield: 12.3 g (~100%) of 3,3,5,7-tetrachloro-1,2,3,4-tetrahydroquinoline-2,4-dione as yellowish crystals; m.p. 248°–254° C. (dec.).

b) 2.83 g (0.123 mol) of sodium were dissolved in 60 ml of methanol while gassing with argon. A solution of 12.3 g (0.040 mol) of 3,3,5,7-tetrachloro-1,2,3,4-tetrahydroquinoline-2,4-dione in 300 ml of methanol was added dropwise thereto at reflux within 10 minutes. The mixture was boiled under reflfux for 10 minutes, treated with 120 ml of 2N aqueous sodium hydroxide solution and distilled until an internal temperature of 100° C. had been achieved. The mixture was cooled, extracted with ethyl acetate and chromatographed over silica gel with toluene/ethyl acetate 19:1 as the eluent. Yield: 4.76 g (43%) of 1-(2-amino-4,6-dichloro-phenyl)-2,2-dimethoxy-ethanone as a red-orange coloured, viscous oil.

MS: me/e (% base peak)=232 (1.0), 200 (6.4), 188 (6.0), 160 (2.0), 124 (6.5), 75 (100).

c) 4.76 g (0.018 mol) of 1-(2-amino-4,6-dichloro-phenyl)-2,2-dimethoxy-ethanone were dissolved in 50 ml of dichloromethane and treated with 2.2 g (0.022 mol) of triethylamine. 3.3 g (0.022 mol) of ethylmalonyl chloride were added dropwise at 0° C. within 10 minutes. The mixture was left to stand at room temperature for 16 hrs., treated with 50 ml of water and extracted with dichloromethane. The crude product was dissolved in 50 ml of ethanol and added dropwise within 15 minutes at reflux to a solution of 1.24 g (0.054 mol) of sodium in 60 ml of ethanol. The mixture was boiled under reflux for 1 hr., concentrate, treated with water, extracted with ethyl acetate and chromatographed over silica gel with dichloromethane/n-hexane 9:1. The product was recrystallized from ether/n-hexane. Yield: 3.58 g (55%) of ethyl 5,7-dichloro-4-dimethoxymethyl-2-hydroxy-quinoline-3-carboxylate as whitish crystals; m.p. 167°–170° C.

d) 5.0 g (0.01 4 mol) of ethyl 5,7-dichloro-4-dimethoxymethyl-2-hydroxy-quinoline-3-carboxylate were suspended in a mixture of 84 ml of acetic acid, 28 ml of water and 14 ml of sulphuric acid and stirred at 100° C. for 16 hrs. The mixture was cooled, treated with 50 ml of water, suction filtered and dried in a vacuum. Yield: 3.88 g (98%) of (RS)-7,9-dichloro-1,4-dihydroxy-1,3-dihydro-furo[3,4-c]quinolin-3-one as white crystals; m.p. 280°–287° C. (dec.).

e) 2.05 g (0.0072 mol) of (RS)-7,9-dichloro-1,4-dihydroxy-1,3-dihydro-furo[3,4-c]quinolin-3-one were dissolved in 20 ml of dimethyl sulphoxide while gassing with argon. 0.36 g (0.0072 mol) of hydrazine hydrate was added thereto and the mixture was stirred at room temperature for 89 hrs. The suspension obtained was treated with ethyl acetate, suction filtered and rinsed with ethyl acetate. Yield: 0.62 g (31%) of 8,10-dichloro-5-hydroxy-3,4-dihydro-pyridazino[4,5-c]quinolin-4-one as beige crystals; m.p. >350° C.

MS: me/e (% base peak)=281 ($C_{11}H_5Cl_2N_3O_2^+$, 100), 253 (92), 213 (14), 197 (17), 162 (29), 57 (42).

EXAMPLE 47

4-Hydroxy-2,3-dihydro-1H-pyrazolo[4,3-c]quinolin-3-one a) 5.35 g (0.22 mol) of magnesium shavings were treated with a mixture of 5 ml of methanol and 0.5 ml of carbon tetrachloride while gassing with argon. After commencement of the reaction 75 ml of ether were cautiously added dropwise thereto. A mixture of 35.2 g (0.22 mol) of diethyl malonate, 20 ml of ethanol and 20 ml of ether was then added dropwise in such a manner that the reaction mixture boiled under reflux slightly. After stirring under reflux for a further 2½ hrs. 37.1 g (0.20 mol) of 2-nitrobenzoyl chloride in 130 ml of ether were then added dropwise. The mixture was boiled under reflux for 1 hr., cooled to 0° C., 250 ml of 2N aqueous sulphuric acid were slowly added dropwise thereto, the mixture was stirred for 20 minutes, extracted with ether, concentrated and dried at 120° C. in a high vacuum. Yield: 53.7 g (86%) of diethyl 2-(2-nitro-benzoyl)malonate as an orange coloured liquid.

MS: me/e (% base peak)=309 ($C_{14}H_{15}NO_7^+$, 0.3), 264 (2.5), 263 (2.3), 217 (3.7), 205 (5.3), 189 (8), 159 (13), 150 (100), 135 (21), 104 (19), 76 (19), 51 (22), 44 (19), 29 (46).

b) A freshly prepared diazomethane solution (~0.038 mol in 150 ml of ether) was added dropwise within 2 minutes to a solution of 9.90 g (0.032 mol) of diethyl 2-(2-nitro-benzoyl)malonate in 150 ml of ether at 5° C. The yellow solution was left to stand at room temperature for 2 hrs, the excess diazomethane was destroyed with 2 g of benzoic acid, the mixture was concentrated and chromatographed over silica gel with toluene/ethyl acetate 9:1 as the eluent. The product was distilled in a bulb tube (b.p. 210°–220° C./0.005 Torr) and recrystallized from ether/n-hexane at −40° C. Yield: 9.0 g (87%) of diethyl (2-[methoxy-(2-nitrophenyl)-methylene]-malonate as white crystals; m.p. 73°–74° C.

c) 3.23 g (0.010 mol) of diethyl (2-[methoxy-(2-nitrophenyl)methylene]-malonate were dissolved in 70 ml of hot ethanol. 1.1 g (0.022 mol) of hydrazine hydrate were added dropwise to the cooled solution. The mixture was boiled under reflux for 2 hrs., a further 1.1 g (0.022 mol) of hydrazine hydrate were added thereto, the mixture was boiled under reflux for 2 hrs. and concentrated totally. The oil obtained was taken up in 100 ml of ethyl acetate, boiled at reflux and cooled. The suspension obtained was suction filtered. The filter cake was taken up in 100 ml of water, adjusted to pH 2 with ~10 ml of 1N aqueous hydrochloric acid and the precipitated product was filtered off under suction. The product was recrystallized from ethanol/water. Yield: 1.93 g (70%) of ethyl 5-(2-nitro-phenyl)-3-oxo-2,3-dihydro-1H-pyrazole-4-carboxylate as white crystals; m.p. 183°–185° C.

d) A solution of 0.55 g (0.002 mol) of ethyl 5-(2-nitrophenyl)-3-oxo-2,3-dihydro-1H-pyrazole-4-carboxylate in 40 ml of ethanol was treated with 50 mg of 10% Pd/C and hydrogenated for 1½ hrs. at room temperature under normal pressure. The catalyst was filtered off, the filtrate was concentrated and the residue was recrystallized from ethyl acetate/n-hexane. Yield: 0.34 g (69%) of ethyl 5-(2-amino-phenyl)-3-oxo-2,3-dihydro-1 H-pyrazole-4-carboxylate as white crystals; m.p. >350° C.

MS: me/e (% base peak)=247 ($C_{12}H_{13}N_3O_3^+$, 18), 201 (100), 145 (36), 144 (33), 117 (56), 89 (30).

e) 0.25 g (0.001 mol) of ethyl 5-(2-amino-phenyl)-3-oxo-2,3-dihydro-1H-pyrazole-4-carboxylate were dissolved in 2.5 ml of dimethylformamide and boiled under reflux for 2 hrs. The mixture was cooled, treated with 20 ml of ethyl acetate, suction filtered and dried in a vacuum. Yield: 0.14 g (70%) of 4-hydroxy-2,3-dihydro-1H-pyrazolo[4,3-c]quinolin-3-one as beige crystals; m.p. >350° C.

MS: me/e (% base peak)=201 ($C_{10}H_7N_3O_2^+$, 100), 145 (27), 144 (32), 127 (7), 117 (33), 116 (24), 89 (21), 69 (17), 57 (21) 43 (22).

EXAMPLE 48

7-Chloro-4-hydroxy-2,3-dihydro-1H-pyrazolo[4,3-c]quinolin-3-one a) 3.52 g (0.145 mol) of magnesium shavings were treated with 3.5 ml of ethanol and 0.35 ml of carbon tetrachloride while gassing with argon. After commencement of the reaction 50 ml of ether were cautiously added dropwise thereto. A mixture of 23.3 g (0.145 mol) of diethyl malonate, 15 ml of ethanol and 15 ml of ether was then added dropwise in such a manner that the reaction mixture boiled slightly. After stirring under reflux for 3 hrs. 25.8 g (0.12 mol) of 4-chloro-2-nitrobenzoyl chloride in 60 ml of ether were then added dropwise. The mixture was boiled under reflux for 1 hr., cooled to 0° C., 150 ml of 2N aqueous hydrochloric acid were slowly added dropwise thereto, the mixture was stirred for 10 minutes, extracted with ether and concentrated. The oily residue was recrystallized from ether/n-hexane at −78° C. Yield: 36.6 g (91%) of diethyl 2-(4-chloro-2-nitro-benzoyl)-malonate as white crystals; m.p. 43°–45° C.

b) A freshly prepared diazomethane solution (~0.034 mol in 150 ml of ether) was added within 2 minutes to a solution of 10.3 g (0.030 mol) of diethyl 2-(4-chloro-2-nitro-benzoyl)malonate in 150 ml of ether at 5° C. The yellow solution was stirred at 5° C. for 1 hr., boiled at reflux for 10 minutes and concentrated totally. Yield: 10.8 g (100%) of diethyl (2-[(4-chloro-2-nitro-phenyl)-methoxy-methylene]-malonate as a yellowish viscous oil.

MS: me/e (% base peak)=312 (17), 297 (5), 239 (5), 237 (13), 225 (2), 186 (10), 180 (11), 154 (13), 138 (11), 125 (19), 112 (9), 99 (5), 87 (6), 75 (9), 59 (10), 29 (100).

c) 10.7 g (0.030 mol) of diethyl (2-[(4-chloro-2-nitro-phenyl)methoxy-methylene]-malonate were dissolved in 200 ml of ethanol and treated with 6.0 g (0.12 mol) of hydrazine hydrate. The mixture was boiled under reflux for 1 hr. and concentrated totally. The oil was dissolved in 400 ml of water, adjusted to pH 1 with ~30 ml of 25% aqueous hydrochloric acid, treated with 1.5 l of ethyl acetate, filtered off, extracted with ethyl acetate and concentrated. The product was recrystallized from hot ethyl acetate. Yield: 5.2 g (56%) of ethyl 5-(4-chloro-2-nitro-phenyl)-3-oxo-2,3-dihydro-1H-pyrazole-4-carboxylate as white crystals; m.p. 230°–235° C. (dec.).

d) A solution of 5.2 g (0.017 mol) of ethyl 5-(4-chloro-2-nitro-phenyl)-3-oxo-2,3-dihydro-1H-pyrazole-4-carboxylate in 300 ml of tetrahydrofuran was treated with 520 mg of 10 percent Pd/C and hydrogenated for 21 hrs. at room temperature under normal pressure. The catalyst was filtered off, the filtrate was concentrated and the residue was recrystallized from ethyl acetate/n-hexane. Yield: 3.1 g (66%) of ethyl 5-(2-amino-4-chloro-phenyl)-3-oxo-2,3-dihydro-1H-pyrazole-4-carboxylate as white crystals; m.p. >350° C.

MS: me/e (% base peak)=281 ($C_{12}H_{12}ClN_3O_3^+$, 11), 235 (100), 206 (2), 178 (24), 151 (35), 123 (12), 114 (9), 89 (12), 45 (14), 31 (27).

e) 3.1 g (0.011 mol) of ethyl 5-(2-amino-4-chloro-phenyl)-3-oxo-2,3-dihydro-1H-pyrazole-4-carboxylate were dissolved in 30 ml of dimethylformamide and boiled under reflux for 2 hrs. The mixture was concentrated, the residue was suspended in 150 ml of methanol at reflux, cooled, suction filtered and dried in a vacuum. Yield: 1.1 g (42%) of 7-chloro-4-hydroxy-2,3-dihydro-1H-pyrazolo[4,3-c]quinolin-3-one as brownish crystals; m.p. >350° C.

MS: me/e (% base peak)=235 ($C_{10}H_6ClN_3O_2^+$, 100), 201 (2), 179 (26), 178(34), 151 (42), 123(17), 114(14), 89(15).

EXAMPLE 49

7,8-Dichloro-4-hydroxy-2,3-dihydro-1H-pyrazolo[4,3-c]quinolin-3-one a) 1.95 g (0.080 mol) of magnesium shavings were treated with 1.95 ml of ethanol and 0.195 ml of carbon tetrachloride. After commencement of the reaction 30 ml of ether were cautiously added dropwise thereto. A mixture of 1.28 g (0.080 mol) of diethyl malonate, 8 ml of ethanol and 9 ml of ether was then added dropwise in such a manner that the reaction mixture boiled slightly. After stirring under reflux for 2 hours 19.5 g (0.072 mol) of 4,5-dichloro-2-nitrobenzoyl chloride in 30 ml of ether were then added dropwise. The mixture was boiled under reflux for 1 hr., cooled to 0° C., 75 ml of 2N aqueous hydrochloric acid were slowly added dropwise, the mixture was stirred for 15 minutes, extracted with ether and concentrated. The crystalline residue was recrystallized from hot ethanol. Yield: 17.9 g (65%) of diethyl 2-(4,5-dichloro-2-nitro-benzoyl)malonate as whitish crystals; m.p. 93°–94° C.

b) A freshly prepared diazomethane solution (~0.052 mol in ether) was added within 2 minutes to a solution of 17.9 g (0.047 mol) of diethyl 2-(4,5-dichloro-2-nitro-benzoyl)-malonate in 350 ml of ether at 5° C. The yellow solution was stirred at 5° C. for ½ hr., boiled at reflux for 10 minutes and concentrated totally. Yield: 18.6 g (100%) of diethyl (2-[(4,5-dichloro-2-nitro-phenyl)-methoxy-methylene]-malonate as a yellow viscous oil.

MS: me/e (ISP)=392.2 ($C_{15}H_{15}Cl_2NO_7.H^+$).

c) 18.6 g (0.047 mol) of diethyl (2-[(4,5-dichloro-2-nitro-phenyl)-methoxy-methylene]-malonate were dissolved in 400 ml of ethanol and treated with 9.5 g (0.19 mol) of hydrazine hydrate. The mixture was boiled under reflux for 1 hr. and concentrated totally. The residue was suspended in 200 ml of ethyl acetate, filtered off under suction and dissolved in 2 l of water. Subsequently, the mixture was adjusted to pH 1 with 2N aqueous hydrochloric acid and the precipitated product was filtered off under suction, dissolved in hot ethyl acetate and recrystallized by the addition of n-hexane at 0° C. Yield: 11.8 g (72%) of ethyl 5-(4,5-dichloro-2-nitro-phenyl)-3-oxo-2,3-dihydro-1H-pyrazole-4-carboxylate as light beige crystals; m.p. 156°–158° C.

d) A solution of 5.0 g (0.014 mol) of ethyl 5-(4,5-dichloro-2-nitro-phenyl)-3-oxo-2,3-dihydro-1H-pyrazole-4-carboxylate in 200 ml of ethyl acetate was treated with 0.5 g of 10% Pd/C and hydrogenated for 6 hrs. at room temperature under normal pressure. The catalyst was filtered off, the filtrate was concentrated and the residue was recrystallized from ethyl acetate/n-hexane. Yield: 3.55 g (78%) of ethyl 5-(2-amino-4,5-dichloro-phenyl)-3-oxo-2,3-dihydro-1H-pyrazole-4-carboxylate as white crystals; m.p. 170°–175° C. (dec.).

e) 0.63 g (0.002 mol) of ethyl 5-(2-amino-4,5-dichlorophenyl)-3-oxo-2,3-dihydro-1H-pyrazole-4-carboxylate was dissolved in 10 ml of dimethylformamide and boiled under reflux for ½ hr. The mixture was cooled, the suspension was treated with 50 ml of ethanol, suction filtered and dried in a vacuum. Yield: 0.18 g (33%) of 7,8-dichloro-4-hydroxy-2,3-dihydro-1H-pyrazolo[4,3-c]quinolin-3-one as beige crystals; m.p. >350° C.

MS: me/e (% base peak)=269 ($C_{10}H_5Cl_2N_3O_2^+$, 100), 213 (31), 185 (36), 157 (12), 150 (15), 125 (11), 73 (48), 44 (68).

EXAMPLE 50

4-Hydroxy-7,8-dimethyl-2,3-dihydro-1H-pyrazolo[4,3-c]quinolin-3-one a) 2.96 g (0.122 mol) of magnesium shavings were treated with 3 ml of ethanol and 0.3 ml of carbon tetrachloride while gassing with argon. After commencement of the reaction 90 ml of ether were cautiously added dropwise thereto. A mixture of 19.5 g (0.122 mol) of diethyl malonate, 11 ml of ethanol and 14 ml of ether was then added dropwise in such a manner that the reaction mixture boiled slightly. After stirring under reflux for 2½ hrs. 24.5 g (0.106 mol) of 4,5-dimethyl-2-nitro-benzoyl chloride, prepared by treating 4,5-dimethyl-2-nitro-benzoic acid (A. Courtin, H. R. von Tobel, Helv. Chim. Acta 1980, 63, 385) with thionyl chloride, in 300 ml of ether/tetrahydrofuran 2:1 were then added dropwise. The mixture was boiled under reflux for 1 hr., cooled to 0° C., 160 ml of 2N aqueous hydrochloric acid were slowly added dropwise thereto, the mixture was stirred for 10 minutes, extracted with ether and concentrated. The oily residue was recrystallized from ether/n-hexane at −20° C. Yield: 32.7 g (88%) of diethyl 2-(4,5-dimethyl-2-nitro-benzoyl)-malonate as white-beige crystals; m.p. 78°–80° C.

b) A freshly prepared diazomethane solution (~0.070 mol in ether) was added within 2 minutes to a solution of 20.3 g (0.060 mol) of diethyl 2-(4,5-dimethyl-2-nitro-benzoyl)-malonate in 250 ml of ether at 5° C. The yellow solution was stirred at 5° C. for ½ hr., left to stand at room temperature for 16 hrs. and concentrated totally. Yield: 21.5 g (100%) of diethyl 2-(4,5-dimethyl- 2-nitro-phenyl)-methoxy-methylene]-malonate as an orange coloured oil.

MS: me/e (% base peak)=306 ($C_{17}H_{21}NO_7^+$, 13), 231 (38), 189 (7), 188 (7), 174 (14), 188 (8), 148 (z7), 119 (47), 106 (25), 91 (21), 77 (20), 29 (100).

c) 21.5 g (0.06 mol) of diethyl 2-(4,5-dimethyl-2-nitro-phenyl)-methoxy-methylene]-malonate were dissolved in 200 ml of ethanol and treated with 12.3 g (0.245 mol) of hydrazine hydrate. The mixture was boiled under reflux for 2 hrs., cooled to 0° C. and the suspension was suction filtered. The crystals were dissolved in 1 l of water. Subsequently, the mixture was adjusted to pH 1 with 1N aqueous hydrochloric acid and the precipitated product was filtered off under suction. Yield: 15.8 g (86%) of ethyl 5-(4,5-dimethyl-2-nitro-phenyl)-3-oxo-2,3-dihydro-1H-pyrazole-4-carboxylate as white-beige crystals; m.p. 166°–167° C.

d) A solution of 15.8 g (0.051 mol) of 5-(4,5-dimethyl-2-nitro-phenyl)-3-oxo-2,3-dihydro-1H-pyrazole-4-carboxylate in 450 ml of ethanol was treated with 1.6 g of 10% Pd/C and hydrogenated for 17 hrs. at room temperature under normal pressure. The mixture was boiled at reflux, the catalyst was filtered off from the hot mixture, the filtrate was concentrated and the residue was recrystallized from ethyl acetate/n-hexane. Yield: 9.40 g (66%) of ethyl 5-(2-amino-4,5-dimethyl-phenyl)-3-oxo-2,3-dihydro-1H-pyrazole-4-carboxylate as whitish crystals; m.p. >350° C.

MS: me/e (% base peak)=275 ($C_{14}H_{17}N_3O_3^+$, 12), 229 (100), 214 (14), 172 (24), 158 (16), 144 (12), 130 (9), 115 (11), 69 (13), 45 (17), 31 (32).

e) 4.2 g (0.015 mol) of ethyl 5-(2-amino-4,5-dimethylphenyl)-3-oxo-2,3-dihydro-1H-pyrazole-4-carboxylate were dissolved in 50 ml of dimethylformamide and boiled under reflux for ½ hr. The mixture was cooled, the suspension was treated with 50 ml of ethanol, suction filtered and dried in a vacuum. Yield: 3.0 g (86%) of 4-hydroxy-7,8-dimethyl-2,3-dihydro-1H-pyrazolo[4,3-c]quinolin-3-one as white crystals; m.p. >350° C.

MS: me/e (% base peak)=229 ($C_{12}H_{11}N_3O_2^+$, 100), 214 (14), 172 (27), 158 (20), 144 (14), 130 (9), 115 (12).

EXAMPLE 51

4-Hydroxy-7-methoxy-2,3-dihydro-1H-pyrazolo[4,3-c]quinolin-3-one a) 3.07 g (0.127 mol) of magnesium shavings were treated with 3 ml of ethanol and 0.3 ml of carbon tetrachloride while gassing with argon. After commencement of the reaction 100 ml of ether were cautiously added dropwise thereto. A mixture of 20.3 g (0.127 mol) of diethyl malonate, 11.5 ml of ethanol and 14.5 ml of ether was then added dropwise in such a manner that the reaction mixture boiled slightly. After stirring under reflux for 2½ hrs. 26.1 g (0.12 mol) of 4-methoxy-2-nitrobenzoyl chloride in 100 ml of tetrahydrofuran were then added dropwise. The mixture was boiled under reflux for ¼ hr., cooled to 0° C., 160 ml of 2N aqueous hydrochloric acid were slowly added dropwise, the mixture was stirred for 15 minutes, extracted with ether, concentrated and chromatographed over silica gel with dichloromethane as the eluent. Yield: 33 g (85%) of diethyl 2-(4-methoxy-2-nitro-benzoyl)-malonate as a deep orange coloured oil.

MS: me/e (% base peak)=293 (2), 247 (8), 219 (12), 180 (65), 134 (23), 106 (43), 63 (54), 29 (100).

b) A freshly prepared diazomethane solution (~0.10 mol in ether) was added within 2 minutes to a solution of 33 g (0.097 mol) of diethyl 2-(4-methoxy-2-nitro-benzoyl)-malonate in 200 ml of ether at 5° C. The solution was stirred at room temperature for 2 hrs. and concentrated totally. Yield: 34 g (~100%) of diethyl (2-[(4-methoxy-2-nitro-phenyl)-methoxy-methylene]-malonate as an orange coloured oil.

MS: me/e (% base peak)=353 ($C_{16}H_{19}NO_8^+$, 2), 308 (21), 233 (29), 189 (14), 176 (16), 150 (24), 121 (29), 106 (22), 77 (12), 63 (14), 29 (100).

c) 34 g (0.097 mol) of diethyl (2-[(4-methoxy-2-nitro-phenyl)-methoxy-methylene]-malonate were dissolved in 400 ml of ethanol and treated with 19.4 g (0.387 mol) of hydrazine hydrate. The mixture was boiled under reflux for 1½ hrs., cooled to 0° C. and concentrated to a volume of ~200 ml. The crystals resulting therefrom were cooled, filtered off under suction and dissolved in ¾ l of water. Subsequently, the mixture was adjusted to pH 2 with 1N aqueous hydrochloric acid and the precipitated product was filtered off under suction. Yield: 22.9 g (77%) of ethyl 5-(4-methoxy-2-nitro-phenyl)-3-oxo-2,3-dihydro-1H-pyrazole-4-carboxylate as white-yellowish crystals; m.p. 205°–210° C.

d) 22.8 g (0.074 mol) of ethyl 5-(4-methoxy-2-nitro-phenyl)-3-oxo-2,3-dihydro-1H-pyrazole-4-carboxylate were dissolved in 2 l of hot ethanol, treated with 2.2 g of 10% Pd/C and hydrogenated for 6 hrs. at 40° C. under normal pressure. The catalyst was filtered off and the filtrate was concentrated totally. Yield: 19 g (91%) of ethyl 5-(2-amino-4-methoxy-phenyl)-3-oxo-2,3-dihydro-1H-pyrazole-4-carboxylate as white-yellowish crystals; m.p. >350° C.

MS: me/e (% base peak)=277 ($C_{13}H_{15}N_3O_4^+$, 13), 231 (100), 188 (18), 174 (17), 147 (10), 132 (14).

e) 5.8 g (0.021 mol) of ethyl 5-(2-amino-4-methoxy-phenyl)-3-oxo-2,3-dihydro-1H-pyrazole-4-carboxylate were suspended in 60 ml of dimethylformamide and boiled under reflux for ½ hr. The mixture was cooled, the suspension was treated with 120 ml of ethanol, suction filtered and dried in a vacuum. Yield: 4.5 g (93%) of 4-hydroxy-7-methoxy-2,3-dihydro-1H-pyrazolo[4,3-c]quinolin-3-one as white-yellowish crystals; m.p. >350° C.

MS: me/e (% base peak)=231 ($C_{11}H_9N_3O_3^+$, 100), 188 (27), 174 (20), 146 (14), 132 (18), 104 (8), 77 (11), 69 (14), 43 (16).

EXAMPLE 52

4-Hydroxy-2,3-dihydro-1H-pyrrolo[3,4-c]quinolin-3-one a) A solution of 1.03 g (0.0058 mol) of 1-(2-aminophenyl)-2-azido-ethanone (J. H. Boyer, D. Straw, *J. Am. Chem. Soc.* 1953, 75, 1642, 2683) in 25 ml of dichloromethane was treated with 0.53 g (0.0053 mol) of triethylamine while gassing with argon. 0.76 g (0.005 mol) of ethylmalonyl chloride was added dropwise at 0° C. and the mixture was stirred at 0° C. for 5 minutes, at room temperature for ½ hr. and at reflux for 2½ hrs. The mixture was cooled to room temperature, poured into dilute aqueous hydrochloric acid, extracted with dichloromethane and concentrated totally. The residue was dissolved in 30 ml of hot toluene, 3 drops of piperidine were added thereto and the mixture was boiled under reflux for 2 hrs. The mixture was cooled to 0° C. and the resulting suspension was suction filtered. The product was recrystallized from hot ethyl acetate. Yield: 0.88 g (56%) of 25 ethyl 4-azidomethyl-2-hydroxy-quinoline-3-carboxylate as white crystals; m.p. 195°–197° C. (dec.).

b) 0.27 g (0.0010 mol) of 4-azidomethyl-2-hydroxy-quinoline-3-carboxylate was dissolved in 20 ml of hot dimethylformamide and treated with 14 mg of 10% Pd/C. A stream of hydrogen was introduced slowly during 1½ hrs. The suspension was filtered under argon and the filtrate was partially concentrated under a high vacuum. The residue was treated with 25 ml of de-gassed ethanol, filtered off, dried in a vacuum and there were obtained ~60 mg (30%) of 4-hydroxy-2,3-dihydro-1H-pyrrolo[3,4-c]quinolin-3-one as an air-sensitive, grey solid. The mother liquor was concentrated totally. The residue was dissolved in 75 ml of methanol and a stream of oxygen was conducted in slowly during 2½ hrs. The mixture was filtered, concentrated, chromatographed over silica gel with ethyl acetate/methanol 9:1 as the eluent and the product was recrystallized from hot ethyl acetate. Yield: 0.033 g (15%) of 4-hydroxy-2,3-dihydro-1H-pyrrolo[3,4-c]-quinoline-1,3-dione as yellow crystals; m.p. 340°–350° C. (dec., subl.).

MS: m/e (% base peak)=214 ($C_{11}H_6N_2O_3^+$, 100), 186 (9), 171 (18), 158 (7), 143 (33), 115 (34), 88 (14), 58 (16).

EXAMPLE 53

7-Chloro-4-hydroxy-2,3-dihydro-1H-pyrrolo[3,4-c]quinoline-1,3-dione a) 8.9 g (0.032 mol) of 2-bromo-1-(4-chloro-2-nitrophenyl)ethanone (prepared analogously to 2-bromo-1-(2-nitrophenyl)ethanone in: P. Ruggli, H. Reichwein, *Helv. Chem. Acta* 1937, 20, 913) were dissolved in 66 ml of sulphuric acid at 50° C. 7.78 g (0.12 g atom) of copper powder were added portionwise thereto in such a manner that the temperature was maintained at about 50° C. The mixture was stirred at 50° C. for 15 minutes, poured on to ice, water was added to a volume of 510 ml, the mixture was extracted with ether and concentrated. The residue was recrystallized from isopropyl ether. Yield: 6.26 g (79%) of 1-(2-amino-4-chloro-phenyl)-2-bromo-ethanone as beige crystals; m.p. 112°14 114° C.

b) A solution of 0.54 g (0.0084 mol) of sodium azide in 50 ml of methanol was added at 0° C. to a solution of 1.98 g (0.008 mol) of 1-(2-amino-4-chloro-phenyl)-2-bromo-ethanone in 40 ml of methanol. The mixture was stirred at 0° C. for ½ hr., at room temperature for ½ hr. and at reflux for 1 hr., cooled, poured into water and extracted with ether. The product was recrystallized from ether/n-hexane. Yield: 1.47 g (87%) of 1-(2-amino-4-chloro-phenyl)-2-azido-ethanone as beige crystals; m.p. 107°–108° C.

c) A solution of 3.92 g (0.01 8 mol) of 1-(2-amino-4-chlorophenyl)-2-azido-ethanone in 150 ml of dichloromethane was treated with 3.76 g (0.037 mol) of triethylamine while gassing with argon. 4.2 g (0.028 mol) of ethylmalonyl chloride was added dropwise at 0° C. and the mixture was stirred at 0° C. for 5 minutes, at room temperature for ½ hr. and at reflux for 24 hrs. The mixture was concentrated totally and chromatographed over silica gel with cyclohexane/ethyl acetate 2:1 as the eluent. The product was recrystallized from ether. Yield: 2.26 g (83%) of ethyl 4-azidomethyl-7-chloro-2-hydroxy-quinoline-3-carboxylate as white crystals; m.p. 188°–190° C.

d) 1.0 g (0.0032 mol) of ethyl 4-azidomethyl-7-chloro-2-hydroxy-quinoline-3-carboxylate was dissolved in a mixture of 80 ml of methanol and 20 ml of dimethylformamide and treated with 46 mg of 10% Pd/C. A hydrogen stream was conducted in slowly during 1 hr. The suspension was suction filtered and the filter cake was suspended in dimethylformamide. The suspension was filtered, concentrated, the residue was suspended in methanol and suction filtered. The substance (0.31 g) was suspended in dimethylformamide and an oxygen stream was conducted in slowly during 4 hrs. The mixture was concentrated and the product was recrystallized from dimethylformamide/methanol. Yield: 0.13 g (18%) of 7-chloro-4-hydroxy-2,3-dihydro-1H-pyrrolo[3,4-c]quinoline-1,3-dione as yellow crystals; m.p. >350° C.

MS: m/e (% base peak)=248 ($C_{11}H_5ClN_2O_3^+$, 100), 205 (23), 177 (27), 149 (18), 114 (20).

EXAMPLE 54

7,8-Dichloro-4-hydroxy-2,3-dihydro-1H-pyrrolo[3,4-c]quinoline-1,3-dione a) 9.17 g (0.030 mol) of 2-bromo-1-(4,5-dichloro-2-nitrophenyl)-ethanone (prepared analogously to 2-bromo-1-(2-nitro-phenyl-ethanone in: P. Ruggli, H. Reichwein, *Helv. Chem. Acta* 1937, 20, 913) were dissolved in 100 ml of sulphuric acid at 50° C. 7.13 g (0.112 g atom) of copper powder were added portionwise thereto in such a manner that the temperature was held at about 50° C. The mixture was stirred at 50° C. for 15 minutes, poured on to ice, water was added to a volume of 470 ml, the mixture was extracted with ether, concentrated and chromatographed over silica gel with toluene as the eluent. The product was recrystallized from isopropyl ether. Yield: 6.82 g (54%) of 1-(2-amino-4,5-dichloro-phenyl)-2-bromo-ethanone as yellow crystals; m.p. 122°–123° C.

b) A solution of 1.38 g (0.021 mol) of sodium azide in 60 ml of methanol was added at 0° C. to a solution of 5.75 g (0.020 mol) of 1-(2-amino-4,5-dichloro-phenyl)-2-bromoethanone in 110 ml of methanol. The mixture was stirred at 0° C. for ½ hr., at room temperature for ½ hr. and at reflux for 1½ hrs., cooled, poured into water and extracted with ether. The product was recrystallized from isopropyl ether. Yield: 4.94 g (100%) of 1-(2-amino-4,5-dichloro-phenyl)-2-azido-ethanone as greenish crystals; m.p. 136°–137° C.

c) A solution of 3.78 g (0.015 mol) of 1-(2-amino-4,5-dichloro-phenyl)-2-azido-ethanone in 150 ml of dichloromethane was treated with 3.12 g (0.030 mol) of triethylamine while gassing with argon. 3.48 g (0.023 mol) of ethylmalonyl chloride were added dropwise at 0° C. and the mixture was stirred at 0° C. for 5 minutes, at room temperature for ½ hr. and at reflux for 48 hrs. The mixture was cooled to room temperature, concentrated totally and chromatographed over silica gel with cyclohexane/ethyl acetate 2:1 as the eluent. The product was recrystallized from ethyl acetate. Yield: 2.37 g (55%) of ethyl 4-azidomethyl-6,7- dichloro-2-hydroxy-quinoline-3-carboxylate as beige crystals; m.p. 197°–198° C.

d) 1.0 g (0.003 mol) of ethyl 4-azidomethyl-6,7-dichloro-2-hydroxy-quinoline-3-carboxylate was dissolved in a mixture of 80 ml of methanol and 20 ml of dimethylformamide and treated with 50 mg of 10% Pd/C. A stream of hydrogen was conducted in slowly during 1¼ hrs. The suspension was suction filtered and the filter cake was suspended in dimethylformamide. The mixture was filtered, concentrated, the residue was suspended in methanol and suction filtered. The substance (0.31 g) was suspended in dimethylformamide and an oxygen stream was conducted in slowly during 2 hrs. The mixture was concentrated and the product was recrystallized from dimethylformamide/methanol. Yield: 0.27 g (20%) of 7,8-dichloro-4-hydroxy-2,3-dihydro-1H-pyrrolo[3,4-c]-quinoline-1,3-dione as yellow crystals; m.p. >350° C.

MS: me/e (% base peak)=282 ($C_{11}H_4Cl_2N_2O_3^+$, 100), 239 (18), 211 (29), 183 (15), 148 (24), 92 (10).

EXAMPLE 55

7-Nitro-2,3,4,5-tetrahydroxy-isoxazol[4,5-c]quinoline-3,4-dione a) 7.7 ml of triethylamine (55 mmol) were added dropwise to a suspension of 10.0 g of ethyl 2-amino-4-nitrobenzoate hydrochloride (4.3 mmol) in 100 ml of acetone. Subsequently, 6.55 ml of methylmalonyl chloride (52 mmol) were added. The reaction mixture was left to stir at room temperature for 48 hrs., concentrated and then treated with a solution of 4.2 g of sodium (183 mmol) in 110 ml of ethanol. The reaction mixture was boiled at reflux for 2.5 hrs. After removing the solvent the residue was taken up in 200 ml of water and heated to 60° C. for 1 hr. Subsequently, the mixture was filtered over Dicalite and thereafter the pH value was adjusted to pH=3.5 with 3N HCl. The precipitate which thereby separated was filtered off, washed with water and dried in a high vacuum. There were obtained 7.2 g of ethyl 4-hydroxy-7-nitro-2-oxo-1,2-dihydro-quinoline-3-carboxylate (60%) as beige crystals.

MS: me/e=278 ($M^+$)

b) 4 ml of trimethylsilylhydroxylamine (30 mmol) were sprayed at room temperature into a suspension of 1.38 g of ethyl 4-hydroxy-7-nitro-2-oxo-1,2-dihydro-quinoline-3-carboxylate (5 mmol) in 40 ml of dioxan. After heating to 100° C. all passed slowly into solution. The reaction mixture was left to stir at 90° C. for 20 hrs., cooled to room temperature and the separated voluminous precipitate was filtered off. This was washed with water and dried in a high vacuum. 740 mg of 4,N-dihydroxy-7-nitro-2-oxo-1,2-dihydro-quinoline-3-carboxamide (65%) were obtained as pale beige crystals.

MS: me/e=254 ($M^+$)

c) 200 mg of 4,N-dihydroxy-7-nitro-2-oxo-1,2-dihydroquinoline-3-carboxamide (0.75 mmol) were suspended in 3 ml of tetrahydrofuran and cooled to 0° C. 0.11 ml of thionyl chloride (1.6 mmol) was sprayed in and the mixture was subsequently warmed to room temperature. After stirring for 16 hrs. the tetrahydrofuran was removed and the residue was treated with 3 ml of dioxan. After cooling to 0° C. 0.32 ml of triethylamine (2.25 mmol) was sprayed in. The mixture was then warmed to room temperature and left to stir for 2 hrs. The resulting brown precipitate was filtered off under suction and recrystallized from methanol. 30 mg of 7-nitro-2,3,4,5-tetrahydro-isoxazol-[4,5-c]quinoline-3,4-dione (16%) were obtained as pale brown crystals.

MS: me/e=247 ($M^+$)

EXAMPLE 56

7-Chloro-2,3,4,5-tetrahydroxy-isoxazol[4,5-]quinoline-3,4-dione a) 7.7 ml of triethylamine (55 mmol) were added dropwise to a suspension of 10.0 g of ethyl 2-amino-4-chlorobenzoate hydrochloride (45 mmol) in 100 ml of acetone. Subsequently, 6.8 ml of methylmalonyl chloride (54 mmol) were added. The reaction mixture was left to stir at room temperature for 48 hrs., concentrated and then treated with a solution of 4.2 g of sodium (183 mmol) in 110 ml of ethanol. The reaction mixture was boiled at reflux for 2.5 hrs. After removing the solvent the residue was taken up in 2.00 ml of water and heated to 60° C. for 1 hr. Subsequently, the mixture was filtered over Dicalite and thereafter the pH value was adjusted to pH=3.5 with 3N HCl. The precipitate which thereby separated was filtered off, washed with water and dried in a high vacuum. 6.94 g of 7-chloro-4-hydroxy-2-oxo-1,2-dihydro-quinoline-3-carboxylate (58%) were obtained as beige crystals.

MS: me/e=267 ($M^+$)

b) 2 ml of trimethylsilylhydroxylamine (15 mmol) were sprayed at room temperature into a suspension of 2.64 g of ethyl 7-chloro-4-hydroxy-2-oxo-1,2-dihydro-quinoline-3-carboxylate (10 mmol) in 2.0 ml of dimethylformamide. After heating to 100° C. all passed slowly into solution. The reaction mixture was left to stir at 80° C. for 2 hrs., cooled to room temperature and stirred overnight. After the addition of 6 ml of water a voluminous precipitate separated and was filtered off, washed with water and dried in a high vacuum. 1.48 g of 7-chloro-4,N-dihydroxy-2-oxo-1,2-dihydro-quinoline-3-carboxamide (58%) were obtained as pale beige crystals.

MS: me/e=254 ($M^+$)

c) 1.48 g of 7-chloro-4,N-dihydroxy-2-oxo-1,2-dihydroquinoline-3-carboxamide (5.8 mmol) were suspended in 10 ml of tetrahydrofuran and cooled to 0° C. 0.85 ml of thionyl chloride (11.6 mmol) was sprayed in and the mixture was subsequently warmed to room temperature. After stirring for 1 hr. the tetrahydrofuran was removed and the residue was treated with 20 ml of dioxan. After cooling to 0° C. 2.5 ml of triethylamine (17.4 mmol) were sprayed in, the mixture was then warmed to room temperature and stirred for 2 hrs. The resulting brown precipitate was filtered off under suction, further product being separated from the mother liquor by acidification. After recrystallization from methanol there were obtained 200 mg of 7-chloro-2,3,4,5-tetrahydroxy-isoxazol[4,5-c]quinoline-3,4-dione (15%) as pale brown crystals.

MS: me/e=236 ($M^+$)

EXAMPLE A

Tablets of the following composition are produced in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in the usual manner:

|  | mg/tablet |
| --- | --- |
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/capsule |
| --- | --- |
| Active ingredient | 50 |
| Cryst. Lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound formula

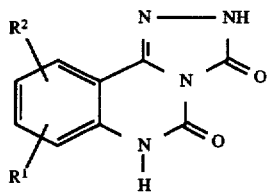
Ia

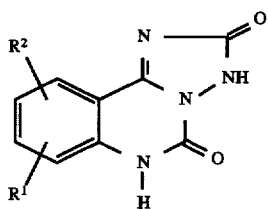
Ib wherein $R^1$ and $R^2$ each independently is hydrogen, lower alkyl, lower alkoxy, nitro, trifluoromethyl, amino, halogen, cyano or $R^3R^4NS(O)_2$— and $R^3$ and $R^4$ are lower alkyl, and $R^2$ can additionally be morpholino or thiomorpholino; a 5- or 6-membered heterocycle with 1–3N atoms, unsubstituted or substituted by lower alkyl, hydroxy, amino or the group —$CH_2NHCH_3$; a bicyclic heterocycle with 1–3N atoms; or a group —$NR^5R^6$ or —$OR^5$ in which $R^5$ and $R^6$ can be the same or different and be hydrogen, lower alkyl, hydroxy-lower alkyl, lower alkoxy-lower alkyl, amino-lower alkyl or lower alkylamino-lower alkyl, as well as pharmaceutically usable salts of compounds of formulas Ia or Ib, excluding 2,3,5,6-tetrahydro-[1,2,4]-triazolo[1,5-c]quinazoline-2,5-dione.

2. A compound according to claim 1, of formula Ia.

3. A compound according to claim 2, wherein $R^1$ and $R^2$ each are hydrogen, halogen, methyl or methoxy.

4. A compound according to claim 2, wherein $R^1$ is nitro and $R^2$ is pyrrolidinyl or dimethylamino.

5. A compound of claim 2, 8-nitro-2,3,5,6-tetrahydro-1,2,4-triazolo[4,3-c]-quinazoline-3,5-dione.

6. A compound of claim 2, 8,9-di-nitro-2,3,5,6-tetrahydro-1,2,4-triazolo[4,3-c]-quinazoline-3,5-dione.

7. A compound of claim 2, 9-bromo-8-nitro-2,3,5,6-tetrahydro-1,2,4-triazolo[4,3-c-]-quinazoline-3,5-dione.

8. A compound of claim 2, 9-fluoro-8-nitro-2,3,5,6-tetrahydro-1,2,4-triazolo[4,3-c]-quinazoline-3,5-dione.

9. A compound of claim 2, 9-chloro-8-nitro-2,3,5,6-tetrahydro-1,2,4-triazolo[4,3-c]-quinazoline-3,5-dione.

10. A compound of claim 2, 9-dimethylamino-8-nitro,2,3,5,6-tetrahydro-1,2,4-triazolo[4,3-c]quinazoline-3,5-dione.

11. A compound according to claim 1, of formula Ib.

12. A compound according to claim 11, wherein $R^1$ is chlorine or imidazolyl and $R^2$ is nitro.

13. A compound according to claim 12, wherein $R^1$ and $R^2$ each are hydrogen, halogen or nitro.

14. A pharmaceutical composition comprising an effective amount of a compound of

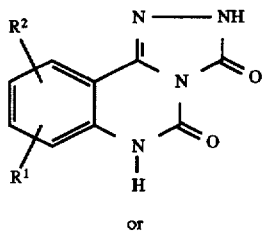
Ia or

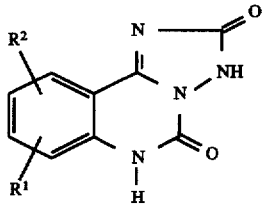
Ib wherein $R^1$ and $R^2$ each independently is hydrogen, lower alkyl, lower alkoxy, nitro, trifluoromethyl, amino, halogen, cyano or $R^3R^4NS(O)_2$— and $R^3$ and $R^4$ are lower alkyl, and $R^2$ can additionally be morpholino or thiomorpholino; a 5- or 6-membered heterocycle with 1–3N atoms, unsubstituted or substituted by lower alkyl, hydroxy, amino or the group —$CH_2NHCH_3$; a bicyclic heterocycle with 1–3N atoms; or a group —$NR^5R^6$ or —$OR^5$ in which $R^5$ and $R^6$ can be the same or different and be hydrogen, lower alkyl, hydroxy-lower alkyl, lower alkoxy-lower alkyl, amino-lower alkyl or lower alkylamino-lower alkyl, as well as pharmaceutically usable salts of compounds of formulas Ia or Ib, excluding 2,3,5,6-tetrahydro-[1,2,4]-triazolo[1,5-c]quinazoline-2,5-dione.

15. A pharmaceutical composition according to claim 14, wherein the compound is a compound of formula Ia.

16. A pharmaceutical composition according to claim 14, wherein the compound is a compound of formula Ib.

\* \* \* \* \*

UNITED STATES PATENT AND TRADEMARK OFFICE
CERTIFICATE OF CORRECTION

PATENT NO. : 5,688,803
DATED : November 18, 1997
INVENTOR(S) : Buttelmann, et al.

It is certified that error appears in the above-identified patent and that said Letters Patent is hereby corrected as shown below:

Claim 1, Column 53, lines 36-53, Formulas Ia & Ib read:

" 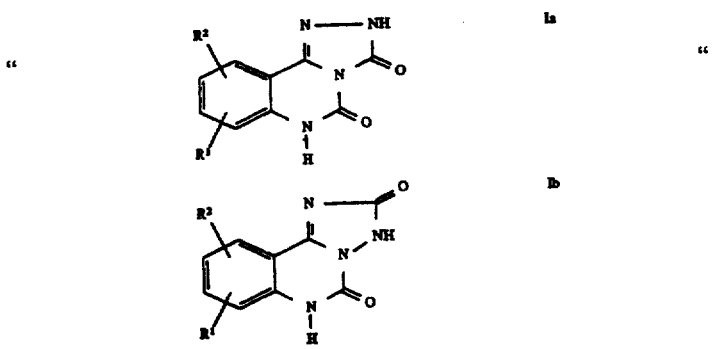 "

UNITED STATES PATENT AND TRADEMARK OFFICE
CERTIFICATE OF CORRECTION

PATENT NO. : 5,688,803
DATED : November 18, 1997
INVENTOR(S) : Buttelmann, et al.

It is certified that error appears in the above-identified patent and that said Letters Patent is hereby corrected as shown below:

Formulas Ia & Ib should read:

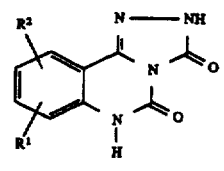

Ia or

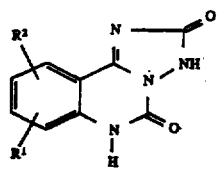

Ib

Signed and Sealed this

Tenth Day of February, 1998

Attest:

BRUCE LEHMAN

Attesting Officer

Commissioner of Patents and Trademarks